US010207047B2

(12) United States Patent
Estes

(10) Patent No.: US 10,207,047 B2
(45) Date of Patent: Feb. 19, 2019

(54) INFUSION PUMP SYSTEM AND METHOD

(71) Applicant: Bigfoot Biomedical, Inc., Milpitas, CA (US)

(72) Inventor: Mark C. Estes, Malibu, CA (US)

(73) Assignee: Bigfoot Biomedical, Inc., Milpitas, CA (US)

(*) Notice: Subject to any disclaimer, the term of this patent is extended or adjusted under 35 U.S.C. 154(b) by 9 days.

(21) Appl. No.: 15/383,176

(22) Filed: Dec. 19, 2016

(65) Prior Publication Data

US 2017/0100536 A1   Apr. 13, 2017

Related U.S. Application Data

(63) Continuation of application No. 13/946,330, filed on Jul. 19, 2013, now Pat. No. 9,561,324.

(51) Int. Cl.
| *A61M 5/142* | (2006.01) |
| *A61M 5/145* | (2006.01) |
| *A61M 5/158* | (2006.01) |
| *G06F 19/00* | (2018.01) |

(Continued)

(52) U.S. Cl.
CPC .... *A61M 5/14244* (2013.01); *A61M 5/14546* (2013.01); *A61M 5/14566* (2013.01); *A61M 5/158* (2013.01); *G06F 19/00* (2013.01); *G06F 19/3418* (2013.01); *G06F 19/3468* (2013.01); *G16H 10/60* (2018.01); *G16H 20/17* (2018.01); *A61M 5/1456* (2013.01); *A61M 2005/14208* (2013.01); *A61M 2005/14268* (2013.01); *A61M 2005/1586* (2013.01); *A61M 2205/3515* (2013.01); *A61M 2205/3569* (2013.01); *A61M 2205/3576* (2013.01); *G05B 2219/31197* (2013.01)

(58) Field of Classification Search
CPC ........ A61M 5/142; A61M 2005/14208; A61M 2005/14256; A61M 2005/1426; A61M 5/172; A61M 2205/3334; G05B 2219/31197
USPC ................................... 604/131, 890.1–891.1
See application file for complete search history.

(56) References Cited

U.S. PATENT DOCUMENTS

| 6,126,595 A | 10/2000 | Amano |
| 6,233,471 B1 | 5/2001 | Berner et al. |
| 6,461,331 B1 | 10/2002 | Van Antwerp |

(Continued)

FOREIGN PATENT DOCUMENTS

| CA | 2543545 | 5/2005 |
| DE | 196 27 619 A | 1/1998 |

(Continued)

OTHER PUBLICATIONS

Collins and Lee, "Microfluidic flow transducer based on the measurement of electrical admittance," *Lab Chip*, 2003, 12 pages.

(Continued)

*Primary Examiner* — Bhisma Mehta
*Assistant Examiner* — William Frehe
(74) *Attorney, Agent, or Firm* — Fish & Richardson P.C.

(57) ABSTRACT

Some embodiments of an infusion pump system may be configured to wirelessly communicate with other devices using near field communication (NFC). In particular embodiments, by incorporating near field communication capabilities into the infusion pump system, user communications with the infusion pump system can be enhanced and simplified.

20 Claims, 6 Drawing Sheets

(51) Int. Cl.
  *G16H 20/17* (2018.01)
  *G16H 10/60* (2018.01)

(56) References Cited

U.S. PATENT DOCUMENTS

| | | |
|---|---|---|
| 6,474,219 B2 | 11/2002 | Klitmose et al. |
| 6,485,461 B1 | 11/2002 | Mason et al. |
| 6,508,788 B2 | 1/2003 | Preuthun |
| 6,524,280 B2 | 2/2003 | Hansen et al. |
| 6,533,183 B2 | 3/2003 | Aasmul et al. |
| 6,537,251 B2 | 3/2003 | Klitmose |
| 6,540,672 B1 | 4/2003 | Simonsen et al. |
| 6,544,229 B1 | 4/2003 | Danby et al. |
| 6,547,764 B2 | 4/2003 | Larsen et al. |
| 6,551,276 B1 | 4/2003 | Mann et al. |
| 6,554,798 B1 | 4/2003 | Mann et al. |
| 6,554,800 B1 | 4/2003 | Nezhadian et al. |
| 6,558,320 B1 | 5/2003 | Causey, III et al. |
| 6,558,351 B1 | 5/2003 | Steil et al. |
| 6,562,001 B2 | 5/2003 | Lebel et al. |
| 6,562,011 B1 | 5/2003 | Buch-Rasmussen et al. |
| 6,564,105 B2 | 5/2003 | Starkweather et al. |
| 6,569,126 B1 | 5/2003 | Poulsen et al. |
| 6,571,128 B2 | 5/2003 | Lebel et al. |
| 6,572,542 B1 | 6/2003 | Houben |
| 6,577,899 B2 | 6/2003 | Lebel et al. |
| 6,582,404 B1 | 6/2003 | Klitgaard et al. |
| 6,585,644 B2 | 7/2003 | Lebel et al. |
| 6,585,699 B2 | 7/2003 | Ljunggreen et al. |
| 6,605,067 B1 | 8/2003 | Larsen |
| 6,613,019 B2 | 9/2003 | Munk |
| 6,641,533 B2 | 11/2003 | Causey, III et al. |
| 6,648,821 B2 | 11/2003 | Lebel et al. |
| 6,650,951 B1 | 11/2003 | Jones et al. |
| 6,656,158 B2 | 12/2003 | Mahoney et al. |
| 6,656,159 B2 | 12/2003 | Flaherty |
| 6,659,948 B2 | 12/2003 | Lebel et al. |
| 6,659,978 B1 | 12/2003 | Kasuga et al. |
| 6,659,980 B2 | 12/2003 | Moberg et al. |
| 6,663,602 B2 | 12/2003 | Møller |
| 6,668,196 B1 | 12/2003 | Villegas et al. |
| 6,669,669 B2 | 12/2003 | Flaherty et al. |
| 6,687,546 B2 | 2/2004 | Lebel et al. |
| 6,690,192 B1 | 2/2004 | Wing |
| 6,691,043 B2 | 2/2004 | Ribeiro, Jr. |
| 6,692,457 B2 | 2/2004 | Flaherty |
| 6,692,472 B2 | 2/2004 | Hansen et al. |
| 6,694,191 B2 | 2/2004 | Starkweather et al. |
| 6,699,218 B2 | 3/2004 | Flaherty et al. |
| 6,702,779 B2 | 3/2004 | Connelly et al. |
| 6,715,516 B2 | 4/2004 | Ohms et al. |
| 6,716,198 B2 | 4/2004 | Larsen |
| 6,723,072 B2 | 4/2004 | Flaherty et al. |
| 6,723,077 B2 | 4/2004 | Pickup et al. |
| 6,733,446 B2 | 5/2004 | Lebel et al. |
| 6,736,796 B2 | 5/2004 | Shekalim |
| 6,740,059 B2 | 5/2004 | Flaherty |
| 6,740,072 B2 | 5/2004 | Starkweather et al. |
| 6,740,075 B2 | 5/2004 | Lebel et al. |
| 6,744,350 B2 | 6/2004 | Blomquist |
| 6,749,587 B2 | 6/2004 | Flaherty |
| 6,752,787 B1 | 6/2004 | Causey, III et al. |
| 6,758,810 B2 | 7/2004 | Lebel et al. |
| 6,768,425 B2 | 7/2004 | Flaherty et al. |
| 6,780,156 B2 | 8/2004 | Haueter et al. |
| 6,786,246 B2 | 9/2004 | Ohms et al. |
| 6,786,890 B2 | 9/2004 | Preuthun et al. |
| 6,796,970 B1 | 9/2004 | Klitmose et al. |
| 6,799,149 B2 | 9/2004 | Hartlaub |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,827,702 B2 | 12/2004 | Lebel et al. |
| 6,830,558 B2 | 12/2004 | Flaherty et al. |
| 6,852,104 B2 | 2/2005 | Blomquist |
| 6,854,620 B2 | 2/2005 | Ramey |
| 6,854,653 B2 | 2/2005 | Eilersen |
| 6,855,129 B2 | 2/2005 | Jensen et al. |
| 6,872,200 B2 | 3/2005 | Mann et al. |
| 6,873,268 B2 | 3/2005 | Lebel et al. |
| 6,878,132 B2 | 4/2005 | Kipfer |
| 6,893,415 B2 | 5/2005 | Madsen et al. |
| 6,899,695 B2 | 5/2005 | Herrera |
| 6,899,699 B2 | 5/2005 | Enggaard |
| 6,922,590 B1 | 7/2005 | Whitehurst |
| 6,936,006 B2 | 8/2005 | Sabra |
| 6,936,029 B2 | 8/2005 | Mann et al. |
| 6,945,961 B2 | 9/2005 | Miller et al. |
| 6,948,918 B2 | 9/2005 | Hansen |
| 6,950,708 B2 | 9/2005 | Bowman, IV et al. |
| 6,960,192 B1 | 11/2005 | Flaherty et al. |
| 6,979,326 B2 | 12/2005 | Mann et al. |
| 6,997,911 B2 | 2/2006 | Klitmose |
| 6,997,920 B2 | 2/2006 | Mann et al. |
| 7,005,078 B2 | 2/2006 | Van Lintel et al. |
| 7,008,399 B2 | 3/2006 | Larson et al. |
| 7,014,625 B2 | 3/2006 | Bengtsson |
| 7,018,360 B2 | 3/2006 | Flaherty et al. |
| 7,025,743 B2 | 4/2006 | Mann |
| 7,029,455 B2 | 4/2006 | Flaherty |
| 7,054,836 B2 | 5/2006 | Christensen et al. |
| 7,104,972 B2 | 9/2006 | Møller et al. |
| 7,128,727 B2 | 10/2006 | Flaherty et al. |
| 7,133,329 B2 | 11/2006 | Skyggebjerg et al. |
| 7,232,423 B2 | 6/2007 | Mernoe et al. |
| 2001/0056262 A1 | 12/2001 | Cabiri |
| 2002/0004651 A1 | 1/2002 | Ljndggreen et al. |
| 2002/0007154 A1 | 1/2002 | Hansen et al. |
| 2002/0040208 A1 | 4/2002 | Flaherty et al. |
| 2002/0091358 A1 | 7/2002 | Klitmose |
| 2002/0126036 A1 | 9/2002 | Flaherty et al. |
| 2003/0055380 A1 | 3/2003 | Flaherty |
| 2003/0065308 A1 | 4/2003 | Lebel et al. |
| 2003/0088238 A1 | 5/2003 | Poulsen |
| 2003/0104982 A1 | 6/2003 | Wittmann et al. |
| 2003/0199825 A1 | 10/2003 | Flaherty |
| 2003/0216683 A1 | 11/2003 | Shekalim |
| 2004/0010207 A1 | 1/2004 | Flaherty et al. |
| 2004/0019325 A1 | 1/2004 | Shekalim |
| 2004/0064088 A1 | 4/2004 | Gorman et al. |
| 2004/0064096 A1 | 4/2004 | Flaherty et al. |
| 2004/0078028 A1 | 4/2004 | Flaherty et al. |
| 2004/0087894 A1 | 5/2004 | Flaherty |
| 2004/0092865 A1 | 5/2004 | Flaherty et al. |
| 2004/0092878 A1 | 5/2004 | Flaherty |
| 2004/0116866 A1 | 6/2004 | Gorman et al. |
| 2004/0127844 A1 | 7/2004 | Flaherty |
| 2004/0153032 A1 | 8/2004 | Garribotto et al. |
| 2004/0171983 A1 | 9/2004 | Sparks et al. |
| 2004/0176727 A1 | 9/2004 | Shekalim |
| 2004/0204673 A1 | 10/2004 | Flaherty |
| 2004/0220551 A1 | 11/2004 | Flaherty et al. |
| 2004/0235446 A1 | 11/2004 | Flaherty et al. |
| 2004/0260233 A1 | 12/2004 | Garibotto et al. |
| 2005/0021005 A1 | 1/2005 | Flaherty et al. |
| 2005/0022274 A1 | 1/2005 | Campbell et al. |
| 2005/0065760 A1 | 3/2005 | Murtfeldt et al. |
| 2005/0090808 A1 | 4/2005 | Malave et al. |
| 2005/0095063 A1 | 5/2005 | Fathallah |
| 2005/0160858 A1 | 7/2005 | Mernoe |
| 2005/0171512 A1 | 8/2005 | Flaherty |
| 2005/0182366 A1 | 8/2005 | Vogt et al. |
| 2005/0192561 A1 | 9/2005 | Mernoe |
| 2005/0203461 A1 | 9/2005 | Flaherty et al. |
| 2005/0215982 A1 | 9/2005 | Estes |
| 2005/0222645 A1 | 10/2005 | Malave et al. |
| 2005/0238507 A1 | 10/2005 | DiIanni et al. |
| 2005/0245878 A1 | 11/2005 | Mernoe et al. |
| 2005/0251097 A1 | 11/2005 | Mernoe |
| 2005/0267402 A1 | 12/2005 | Stewart et al. |
| 2005/0273059 A1 | 12/2005 | Mernoe et al. |
| 2006/0041229 A1 | 2/2006 | Garibotto et al. |

(56) References Cited

U.S. PATENT DOCUMENTS

| | | |
|---|---|---|
| 2006/0069382 A1 | 3/2006 | Pedersen |
| 2006/0074381 A1 | 4/2006 | Malave et al. |
| 2006/0095014 A1 | 5/2006 | Ethelfeld |
| 2006/0135913 A1 | 6/2006 | Ethelfeld |
| 2006/0142698 A1 | 6/2006 | Ethelfeld |
| 2006/0178633 A1 | 8/2006 | Garibotto et al. |
| 2006/0184119 A1 | 8/2006 | Remde et al. |
| 2006/0200073 A1 | 9/2006 | Radmer et al. |
| 2006/0206054 A1 | 9/2006 | Shekalim |
| 2006/0247581 A1 | 11/2006 | Pedersen et al. |
| 2007/0073228 A1 | 3/2007 | Mernoe et al. |
| 2007/0073235 A1 | 3/2007 | Estes et al. |
| 2007/0073236 A1 | 3/2007 | Mernoe et al. |
| 2007/0124002 A1 | 5/2007 | Estes et al. |
| 2007/0156092 A1 | 7/2007 | Estes et al. |
| 2007/0167905 A1 | 7/2007 | Estes et al. |
| 2007/0167912 A1 | 7/2007 | Causey et al. |
| 2008/0103022 A1* | 5/2008 | Dvorak ............... A63B 71/0622 482/3 |
| 2008/0125700 A1 | 5/2008 | Moberg et al. |
| 2008/0172027 A1 | 7/2008 | Blomquist |
| 2008/0198012 A1 | 8/2008 | Kamen |
| 2008/0306444 A1 | 12/2008 | Brister |
| 2008/0319381 A1* | 12/2008 | Yodfat ................. A61M 5/1723 604/65 |
| 2009/0177142 A1 | 7/2009 | Blomquist et al. |
| 2010/0324977 A1* | 12/2010 | Dragt ................. G06Q 30/0257 705/14.1 |
| 2011/0105955 A1 | 5/2011 | Yudovsky et al. |
| 2011/0163880 A1 | 7/2011 | Halff et al. |
| 2011/0199194 A1* | 8/2011 | Waldock ................. B25J 9/1656 340/10.51 |
| 2011/0319813 A1* | 12/2011 | Kamen ............. A61M 5/14244 604/66 |
| 2012/0029468 A1* | 2/2012 | DiPerna ............. A61M 5/1413 604/500 |
| 2012/0185267 A1* | 7/2012 | Kamen .................. G06Q 50/22 705/2 |
| 2012/0238851 A1* | 9/2012 | Kamen ............. A61M 5/14244 600/365 |
| 2012/0323590 A1* | 12/2012 | Udani .................. G06Q 10/103 705/2 |
| 2012/0330270 A1 | 12/2012 | Colton |
| 2013/0165041 A1 | 6/2013 | Bukovjan et al. |
| 2013/0204202 A1* | 8/2013 | Trombly ............... A61M 5/172 604/207 |

FOREIGN PATENT DOCUMENTS

| | | |
|---|---|---|
| DE | 102 36 669 | 2/2004 |
| DE | 20 2005 012 358 | 10/2005 |
| EP | 0 496 141 | 7/1992 |
| EP | 0 612 004 | 8/1994 |
| EP | 0 580 723 | 10/1995 |
| EP | 1 045 146 | 10/2000 |
| EP | 1 136 698 | 9/2001 |
| EP | 1 177 802 | 2/2002 |
| EP | 0 721 358 | 5/2002 |
| EP | 1 495 775 | 1/2005 |
| EP | 1 527 792 | 5/2005 |
| EP | 1 754 498 | 2/2007 |
| EP | 2 764 881 | 8/2014 |
| FR | 2 585 252 | 1/1987 |
| GB | 747 701 | 4/1956 |
| GB | 2 218 831 | 11/1989 |
| WO | WO 1990/15928 | 12/1990 |
| WO | WO 1997/21457 | 6/1997 |
| WO | WO 1998/11927 | 3/1998 |
| WO | WO 1998/57683 | 12/1998 |
| WO | WO 1999/21596 | 5/1999 |
| WO | WO 1999/39118 | 8/1999 |
| WO | WO 1999/48546 | 9/1999 |
| WO | WO 2001/72360 | 10/2001 |
| WO | WO 2001/91822 | 12/2001 |
| WO | WO 2001/91833 | 12/2001 |
| WO | WO 2002/40083 | 5/2002 |
| WO | WO 2002/057627 | 7/2002 |
| WO | WO 2002/100469 | 12/2002 |
| WO | WO 2003/103763 | 12/2003 |
| WO | WO 2004/056412 | 7/2004 |
| WO | WO 2004/093648 | 11/2004 |
| WO | WO 2004/110526 | 12/2004 |
| WO | WO 2005/002652 | 1/2005 |
| WO | WO 2005/039673 | 5/2005 |
| WO | WO 2005/072794 | 8/2005 |
| WO | WO 2005/072795 | 8/2005 |
| WO | WO 2006/075016 | 7/2006 |
| WO | WO 2006/105792 | 10/2006 |
| WO | WO 2006/105793 | 10/2006 |
| WO | WO 2006/105794 | 10/2006 |
| WO | WO 2007/056592 | 5/2007 |
| WO | WO 2008/089184 | 7/2008 |

OTHER PUBLICATIONS

Debiotech News Release, "Debiotech reveals its new miniaturized Disposable Insulin Nanopump™ for Diabetes therapy," available at http://www.debiotech.com/news/nw_159.html Apr. 24, 2006, 3 pages.

Medtronic News Release, "Medtronic Receives FDA Approval for World's First Insulin Pump with Real-time Continuous Glucose Monitoring," Apr. 13, 2006, 3 pages.

Patent Abstracts of Japan, vol. 1999, No. 04, and JP 11 010036 , Apr. 30, 1999 and Jan. 19, 1999, Toray Ind. Inc., 6 pages.

Walsh et al., "Guidelines for Optimal Bolus Calculator Settings in Adults", *J. Diabetes Science and Technology*, Jan. 2011, 5(1):7 pages.

Walsh et al., "Guidelines for Insulin Dosing in Continuous Subcutaneious Insulin Infusion Using New Formulas from a Retrospective Study of Individuals with Optimal Glucose Levels", *J. Diabetes Science and Technology*, Sep. 2010, 4(5):8 pages.

Asante Pearl, Insulin Pump User Manual, 2012, 180 pages.

International Search Report and Written Opinion in International Application No. PCT/US2014/047023, dated Nov. 28, 2014, 19 pages.

International Preliminary Report and Written Opinion in International Application No. PCT/US2014/047023, dated Jan. 19, 2016, 8 pages.

\* cited by examiner

INFUSION PUMP SYSTEM AND METHOD

CROSS-REFERENCE TO RELATED APPLICATIONS

This application is a continuation application of and claims priority to U.S. application Ser. No. 13/946,330, filed on Jul. 19, 2013.

TECHNICAL FIELD

This document relates to an infusion pump system, such as a portable infusion pump system for dispensing a medicine.

BACKGROUND

Pump devices are commonly used to deliver one or more fluids to a targeted individual. For example, a medical infusion pump device may be used to deliver a medicine to a patient as part of a medical treatment. The medicine that is delivered by the infusion pump device can depend on the condition of the patient and the desired treatment plan. For example, infusion pump devices have been used to deliver insulin to the vasculature of diabetes patients so as to regulate blood-glucose levels.

Users of infusion pump devices often need to communicate with the infusion pump via a user interface to control the operations of the infusion pump in a safe and effective manner. For example, a user may press a series of buttons on the user interface to enter food intake data into the infusion pump, such as a number of grams of carbohydrates that is indicative of a recently or soon-to-be consumed meal. The food intake data can be combined by the infusion pump system with other parameters to calculate a suggested bolus dosage of insulin based on the grams of carbohydrates entered by the user. In another example, a user may enter information into the infusion pump system via a user interface that indicates that the user is going to perform a level of physical exercise. In some circumstances, the infusion pump system may reduce the amount of a planned dispensation of insulin in response to the exercise information entered by the user.

SUMMARY

Some embodiments of an infusion pump system may be configured to send and receive data communications using near field communication ("NFC") technology. By incorporating NFC technology within the infusion pump system, user communications with the pump system can be enhanced and simplified. For example, NFC can facilitate the convenient sharing of user commands or other data to an infusion pump system a NFC that is equipped with NFC functionality. In some embodiments, pre-programmed NFC communicator devices ("NFC tags") can be used to transfer data from the NFC tag to the infusion pump system via a simple hand motion or the like by the user of the infusion pump system. The data that is transferred may cause the infusion pump system to execute particular operations as defined by the data or in correspondence to the data. For example, a NFC tag can be configured to communicate a set of user input commands to an infusion pump system (e.g., user input commands that might otherwise be input via a series of menu selections and data entry steps on the user interface of the pump system) so as to rapidly indicate to the pump system that particular amount of food or carbohydrates will be consumed for a meal. In some embodiments, data can be written from the infusion pump system to a NFC tag. For example, a back-up copy of user settings that are used to configure an infusion pump system for a particular user may be downloaded using NFC from the infusion pump system and saved onto a NFC tag. In particular embodiments, the infusion pump system can be equipped with one or more accelerometers that can be used to activate the potential for NFC communications to take place when an acceleration at or above the threshold level is detected.

In particular embodiments, a medical infusion pump system may include a portable pump housing that defines a space to receive a medicine. The infusion pump system may include a pump drive system to dispense medicine from the portable housing when the medicine is received in the space. The infusion pump system may further include control circuitry that communicates control signals to the pump drive system to control dispensation of the medicine from the portable housing when the medicine is received in the space. Optionally, the infusion pump system may also include a near field communication (NFC) circuit electrically connected with the control circuitry to communicate infusion pump task data to the control circuitry. The NFC circuit can be configured to wirelessly receive the infusion pump task data from a NFC communicator device when the NFC circuit and NFC communicator device are positioned with in a NFC proximity range.

In some implementations, the system may optionally include the NFC communicator device that is separate from the pump housing. For example, the NFC communicator device can be a near field communication tag storing the infusion pump task data. The infusion pump task data may comprise a unique identifier that identifies the near field communication tag, and in response to receiving the unique identifier, the control circuitry may execute user interface operations that correspond to the unique identifier. Optionally, the user interface operations may comprise user interface settings for calculating a suggested bolus dispensation of the medicine. In another option, the infusion pump system may further include an accelerometer electrically connected to the control circuitry, wherein the accelerometer may be configured to detect acceleration movement of the portable housing and to communicate the detected movement to the control circuitry. In a further option, the control circuitry is configured to compare a characteristic value of the detected movement to a threshold movement value. The control circuitry may be configured to activate near field communication with the NFC communicator device based on the comparison of the characteristic value to the threshold movement value. Optionally, the control circuitry may be housed in a controller housing that is removably attachable to the portable housing.

In some implementations described herein, the system may optionally include a remote control device that is separate from the pump housing. The remote control device can be configured to wirelessly communicate with a wireless communication device connected to the control circuitry (for example, a wireless communication device that is different from the aforementioned the NFC circuit). Optionally, the remote control device may further include a second NFC circuit that is configured to wirelessly receive the infusion pump task data from the NFC communicator device when the second NFC circuit and NFC communicator device are positioned within the NFC proximity range. In some cases, the NFC proximity range has a maximum working distance of less than 12 inches. The infusion pump task data may be indicative of a value of carbohydrates of a food item.

In particular embodiments, a medical infusion pump system may include a pump device and a controller device. The pump device may include a pump housing that defines a space to receive a medicine, and a drive system positioned in the pump housing to dispense the medicine from the pump device when the medicine is received in the space of the pump housing. Optionally, the controller device may be removably attachable to the pump device. For example, the controller device may be removably attachable to the pump housing so as to electrically connect with the pump device. The controller device may house control circuitry configured to communicate control signals to the drive system positioned in the pump housing to control dispensation of the medicine from the pump device. The controller device may also house a NFC circuit electrically connected with the control circuitry to communicate infusion pump task data to the control circuitry. Optionally, the NFC circuit is configured to wirelessly receive the infusion pump task data from a NFC communicator device when the NFC circuit and NFC communicator device are positioned with in a NFC proximity range.

In some implementations, the system may further comprise the NFC communicator device that is separate from the pump device and the controller device. For example, the NFC communicator device may be a near field communication tag storing the infusion pump task data. Optionally, the infusion pump task data may comprise a unique identifier that identifies the near field communication tag, and in response to receiving the unique identifier, the control circuitry may execute user interface operations that correspond to the unique identifier. In one example, the user interface operations may comprise user interface settings for calculating a bolus dispensation of the medicine. Optionally, the system may further include at least one accelerometer electrically connected to the control circuitry. The accelerometer may be configured to detect acceleration movement of the portable pump housing and to communicate the detected movement to the control circuitry. The control circuitry may be configured to compare a characteristic value of the detected movement to a threshold movement value. The control circuitry may be configured to activate near field communication with the NFC communicator device based on the comparison of the characteristic value to the threshold movement value.

In various implementations of the system, the pump device may optionally be a one-time-use device equipped with one or more structures configured to prevent reuse of the pump device. Also, in some implementations, the controller device may optionally be a reusable controller device. For example, the controller device may include one or more of: a controller housing that is removably attachable to the pump housing in a fixed relationship; one or more electrical contacts disposed on the controller housing, the electrical contacts of the controller device being engageable with corresponding electrical contacts of the pump device when removably attached.

Additionally, particular embodiments described herein may include a method of controlling a portable infusion pump system. The method may include receiving input via near field communication (NFC) from a NFC tag storing data indicative of a task associated with using the portable infusion pump system. The method may optionally include controlling the portable infusion pump system to change an operation of the portable infusion pump system in based upon the data the input from the NFC tag. In some implementations, the method may further comprise prompting a user via a user interface display to confirm the operation change of the portable infusion pump system in response to receiving the input from the NFC tag. For example, the operation change to be confirmed via the user interface may include calculating or initiating a bolus dispensation of a medicine from the portable infusion pump system.

Some or all of the embodiments described herein may provide one or more of the following advantages. First, some embodiments of the infusion pump system may be configured to send and receive data communications using NFC technology. Second, some embodiments of an infusion pump system equipped with NFC technology may facilitate convenient user input of information to the infusion pump system. Third, the safety and efficacy of an infusion pump system may be enhanced because the rapid manner of inputting data to the infusion pump using NFC may facilitate more timely and complete data entry by the user. Fourth, in some circumstances, some users who may not be mentally or physically able to reliably operate a conventional user interface of an infusion pump system may be able to reliably input data to an infusion pump system using NFC communication interface. Fifth, the infusion pump system equipped with NFC equipment may be configured to be portable, wearable, and (in some circumstances) concealable. For example, a user can conveniently wear the infusion pump system on the user's skin under clothing or can carry the pump system in the user's pocket (or other portable location) while receiving the medicine dispensed from the pump device.

It should be understood from the description herein that the term "NFC" (as used herein) or "NFC" capability (as used herein) is different from traditional radio frequency identification ("RFID"). For example, NFC is a more specific version of wireless communication that can be configured for one-way or two-way communications and that operates at a maximum range of less than about 12 inches, about 8 inches or less, and preferably about 4 inches or less (e.g., unlike the much greater communication range of the traditional RFID technology that extends for many feet or more).

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION OF ILLUSTRATIVE EMBODIMENTS

Figure 1:
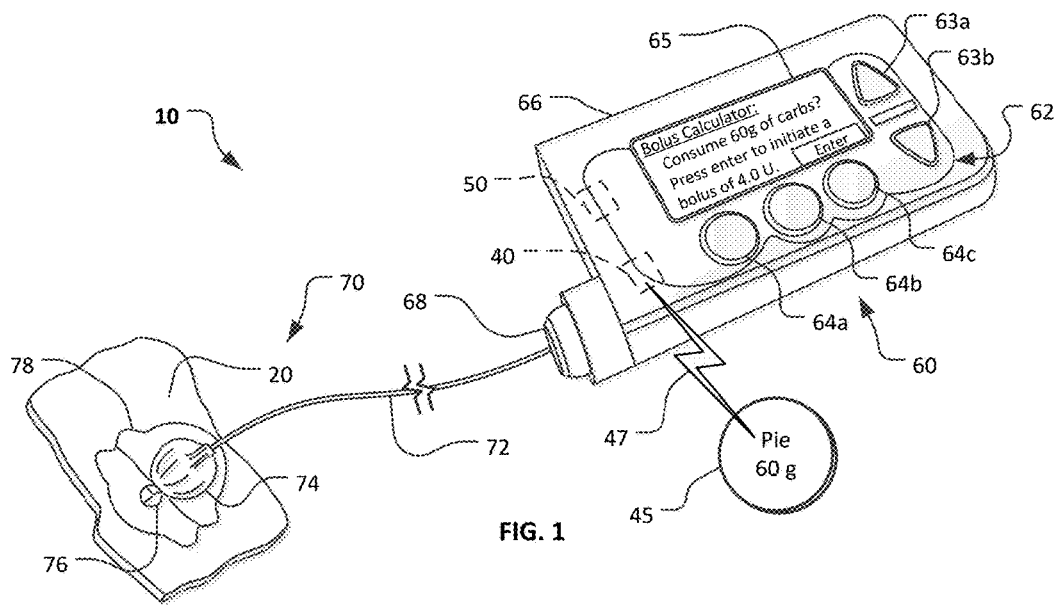
FIG. 1 is a perspective view of an infusion pump system with NFC capabilities in accordance with some embodiments.

Referring to FIG. 1, an infusion pump system 10 can include a portable pump 60 used to supply insulin or another medication to a user via, for example, an infusion set 70. In some embodiments, the portable pump 60 includes a user interface 62 comprised of input devices such as buttons 63a, 63b, 64a, 64b, 64c and output devices such as display 65. At least a portion of the user interface 62 is coupled to a pump housing structure 66 of the portable pump 60, which houses the control circuitry for the portable pump 60. In particular embodiments, the portable pump 60 may further include a NFC circuit 40 that facilitates short-range wireless communications between the internal control circuitry of the portable pump 60 and an external device such as a NFC tag 45.

NFC can be used, for example, to rapidly input user commands or other data into the portable pump 60, thereby at least partially reducing the need to actuate the buttons 63a-63b, 64a-64c or other components of the user interface 62. As explained further herein, the data input to the portable pump 60 via NFC may cause the portable pump 60 to execute particular actions, such as automatically calculating an amount of a recommended bolus delivery of insulin (or another medication) and prompting the user with an option to confirm and initiate such a bolus delivery. By incorporating NFC equipment within the infusion pump system 10, user communications with the portable pump 60 can be enhanced and simplified. As a result, the accuracy and completeness of the data entered by the user into the portable pump 60 can be improved, and the user can experience greater convenience and time efficiency. Optionally, the portable pump 60 can further include an accelerometer 50 arranged in the pump housing structure 66. In some embodiments, the accelerometer 50 can be used to activate the NFC communications when an acceleration at or above the threshold level is detected, as explained further below.

The infusion pump system 10 is configured to controllably dispense a medicine to be infused into the tissue or vasculature of a targeted individual, such as a human or animal patient. In some embodiments, the portable pump 60 includes the housing structure 66 that defines a cavity in which a fluid cartridge (not shown) can be received. For example, the fluid cartridge can be a carpule that is either user-fillable or is preloaded with insulin or another medicine for use in the treatment of Diabetes (e.g., Byetta®, Symlin®, or others). Such a cartridge may be supplied, for example, by Eli Lilly and Co. of Indianapolis, Ind. Other examples of medicines that can be contained in the fluid cartridge include: pain relief drugs, hormone therapy, blood pressure treatments, anti-emetics, osteoporosis treatments, or other injectable medicines. The fluid cartridge may have other configurations. For example, in some embodiments the fluid cartridge may comprise a reservoir that is integral with the pump housing structure 66 (e.g., the fluid cartridge can be defined by one or more walls of the pump housing structure 66 that surround a plunger to define a reservoir in which the medicine is injected or otherwise received).

The portable pump 60 includes a cap device 68 to retain the fluid cartridge in the cavity of the housing structure 66 and, optionally, to penetrate a septum of the fluid cartridge for purposes of establishing fluid communication with the infusion set 70. The portable pump 60 includes a drive system (one example is described in more detail below in connection with FIG. 5) that advances a plunger in the fluid cartridge so as to dispense fluid therefrom. In some embodiments, the dispensed fluid exits the fluid cartridge, passes through a flexible tube 72 of the infusion set 70 to a cannula housing 74 retained to the user's skin 20 by a skin adhesive patch 78. The dispensed fluid can enter through the skin 20 via a cannula 76 attached to the underside of the cannula housing 74.

In some embodiments, the infusion pump system 10 can be configured to supply scheduled basal dosages of insulin (or another medication) along with user-selected bolus dosages. The basal delivery rate can be selected to maintain a user's blood glucose level in a targeted range during normal activity when the user is not consuming food items. The user-selected bolus deliveries may provide substantially larger amounts of insulin in particular circumstances in which the user's blood glucose level requires a significant correction. In some embodiments, the infusion pump system 10 can suggest a bolus dosage to the user in a manner that accounts for the user's food intake, the user's recent blood glucose level (e.g., input into the portable pump 60 by the user, from an integral blood test strip analyzer, transmitted to the portable pump 60 from an external blood glucose monitoring device, or the like), the rate of change in the user's blood glucose level, and previously delivered insulin that has not acted on the user. For example, a user can enter a carbohydrate value indicative of a meal into the portable pump 60, and in response thereto, the portable pump 60 can output a suggested bolus dosage to the user.

In some embodiments, the infusion pump system 10 may modify a bolus delivery (e.g., a bolus delivery after the user consumes a meal) in response to certain circumstances. For example, the infusion pump system 10 may decrease or otherwise modify a post-meal bolus delivery based on a rapidly falling blood glucose level, a current blood glucose level that is below a threshold limit, based on an increased level of physical activity, or the like.

The infusion pump system 10 can be configured to be portable and can be wearable and concealable. For example, a user can conveniently wear the infusion pump system 10 on the user's skin (e.g., using skin adhesive) underneath the user's clothing or carry the portable pump 60 in the user's pocket (or other portable location) while receiving the medicine dispensed from the infusion pump system 10. As such, the pump system 10 can be used to deliver medicine to the tissues or vasculature of the user in a portable, concealable, and discrete manner.

Still referring to FIG. 1, the portable pump 60 includes the user interface 62 that permits a user to monitor and control the operation of the infusion pump system 10. In some embodiments, the user interface 62 includes a display 65 and the user-selectable buttons (e.g., five buttons 63a, 63b, 64a, 64b, and 64c in this embodiment) that are in electrical communication with the control circuitry of the portable pump 60. For example, the display 65 may be used to communicate a number of status indicators, alarms, settings, and/or menu options for the infusion pump system 10. In some embodiments, the user may press one or more of the buttons 63a, 63b, 64a, 64b, and 64c to shuffle through a number of menus or program screens that show particular status indicators, settings, and/or data (e.g., review data that shows the medicine dispensing rate, the amount of medicine delivered during the last bolus, the delivery time of the last bolus, the total amount of medicine dispensed in a given time period, the amount of medicine scheduled to be dispensed at a particular time or date, the approximate amount of medicine remaining in the cartridge, or the like).

In some embodiments, the user can adjust the settings or otherwise program the portable pump 60 by pressing one or more buttons 63a, 63b, 64a, 64b, and 64c of the user interface 62. For example, in embodiments of the infusion pump system 10 configured to dispense insulin, the user may press one or more of the buttons 63a, 63b, 64a, 64b, and 64c to change the dispensation rate of insulin or to request that a bolus of insulin be dispensed immediately, at a scheduled later time, over a period of time, or following a particular time-based profile. In another example, the user may use the buttons 63a, 63b, 64a, 64b, and 64c to manually input information such as the user's current blood glucose level (e.g., as measured by an external blood glucose meter), the current rate of change in the user's blood glucose level, or the like into the portable pump 60.

In some embodiments, the NFC circuit 40 is housed in the portable pump 60 to provide an additional functionality that can enhance and simplify user interactions with the portable pump 60. For instance, using NFC, the need for user activation of multiple buttons 63a, 63b, 64a, 64b, and 64c for shuffling through menus may be eliminated or otherwise reduced in some circumstances. In one example depicted in FIG. 1, the user of infusion pump system 10 has consumed, or will soon consume, a piece of pie that is estimated to include about 60 grams of carbohydrates. As such, the user desires to initiate a corresponding bolus dispensation of insulin to counteract the effects of the intake of 60 grams of carbohydrates. The bolus dispensation of insulin may be intended to cause the user's blood glucose level to remain within a target range.

To initiate the desired bolus dispensation, the user can first position the portable pump 60 containing the NFC circuit 40 in close proximity with the NFC tag 45 (e.g., preferably within a range 4 inches or less, including for example, a physical "bump" with the NFC tag 45). Wireless near field communications can thereby be established between the NFC circuit 40 and the NFC tag 45 (as signified by wireless communication symbol 47). In some embodiments, the user is provided with a notification that near field communications have been established. The notification can be visual, audible, tactile (vibratory), or a combination thereof. In response to the communication between the NFC tag 45 and the portable pump 60, the portable pump 60 provides a prompt to the user on the display 65. The prompt on the display 65 requests the user to confirm that the user desires to receive a 4.0 unit dispensation of insulin related to the intake of 60 grams of carbohydrates. To confirm and initiate the dispensation of the suggested bolus amount, the user can simply press button 64c to select "Enter." By this example, it can be appreciated that the incorporation of NFC equipment in the infusion pump system 10 can enhance and simplify user interactions with the infusion pump system 10, because in order to initiate appropriate suggested bolus dosage of insulin, the user simply bumped the NFC tag 45 with the pump housing 66 and then pressed a single acknowledgement button in response to the prompt on the display 65. As will be described further, in some embodiments other techniques for user confirmation or acknowledgement can be used, and in some instances user confirmation or acknowledgement may be optional.

NFC provides short-range wireless communication. As described herein, the maximum working distance for NFC is less than 12 inches, about 8 inches or less, and about 4 inches or less in the aforementioned embodiment depicted in FIG. 1. NFC allows sharing of relatively small packets of data between a NFC tag and a device equipped with NFC functionality. In the embodiment depicted in FIG. 1, each NFC tag can store about a kilobyte of data or less, although NFC tags that store a greater quantity of data can also be used in the embodiments described herein. The NFC tags can be configured with a shape that is small and lightweight (e.g., a maximum dimension of about 1 inch or less), particular because the NFC tags described the embodiment of FIG. 1 do not have an integral power source such as a battery. Instead, a coil in the NFC tag inductively receives magnetic field energy that is emitted from a coil in NFC circuit housed in the portable infusion pump 66. Accordingly, energy and data can be wirelessly transmitted between the coils of the NCF tag and the device with NFC functionality. The wireless NFC data transmission can be a two-way wireless communication. That is, data can be transmitted from the NFC tag to the NFC circuit of the pump 60, and data can be transmitted to the NFC tag from the NFC circuit of the pump 60. In other words, the NFC circuit of the pump 60 can both read from and write to a NFC tag. The data stored in the NFC tag can be written in a variety of formats. One example format is called the NFC Data Exchange Format ("NDEF").

Referring again to FIG. 1, when the NFC tag 45 communicates with the NFC circuit 40, the resulting data exchange can trigger one or more automated actions by control circuitry housed in the portable pump 60. The particular actions are at least in part defined by particular computer program script that is initiated in response to the communications between the NFC tag 45 and NFC circuit 40. In some arrangements, the particular computer program script is stored on the NFC tag. In such arrangements, when the communications between the NFC tag 45 and NFC circuit 40 are established, the particular computer program script is transferred from the NFC tag 45 to the control circuitry of the portable pump 60 via the NFC circuit 40. The control circuitry then executes the particular computer program script and can cause the portable pump 60 to automatically perform an action or actions in accordance with the script.

In alternative arrangements, the particular computer program script to be executed in correspondence to the NFC tag 45 can be stored within the internal control circuitry of the portable pump 60. In such arrangements, the NFC tag 45 can transfer a unique identifier such as a serial number to the NFC circuit 40. Upon receipt of the unique identifier, the portable pump 60 can execute the particular computer program script that corresponds to the identifier. In some embodiments, a combination of both arrangements can be used. In any case, from the description herein it can be appreciated that a particular NCF tag (e.g., NFC tag 45) can be used to automatically trigger a corresponding particular action or change in operation of the portable pump 60. As such, a variety of NFC tags can be conveniently used with an infusion pump system 10 so as to enhance and simplify user interactions with the infusion pump system 10 in regard to a variety of scenarios and user desires.

In some embodiments, an accelerometer 50 can be optionally positioned in the portable pump 60 and connected to the control circuitry inside the housing structure 66.

In particular embodiments, more than one accelerometer 50 can be included in the housing structure 66. The accelerometer 50 can operate in conjunction with control circuitry and the NFC circuit 40 to supplement the criteria for activating communications between the NFC circuit 40 and the NFC tag 45. In other words, while in some embodiments communications between the NFC circuit 40 and the NFC tag 45 are activated based merely on the proximity therebetween, in other embodiments a threshold movement of the housing structure 66 (as detected by the accelerometer 50) is used (at least as a factor) in activating the NFC circuit 40 for communication with the nearby NFC tag 45. For example, in some embodiments the accelerometer 50 can serve to require that the user "bump" or otherwise tap the portable pump 60 onto the NFC tag 45 or another object before the NFC circuit 40 is activated. An objective for including this feature can be to more clearly ascertain that the user desires to activate NFC when the NFC tag 45 is within the required proximity with the NFC circuit 40. That is, by requiring the user to tap the portable pump 60 onto the NFC tag 45, the user's intentions for activating NFC can be confirmed with a greater level of confidence.

In some embodiments, this optional feature of using the accelerometer 50 in conjunction with the NFC circuit 40 can function as follows. When a movement is detected by accelerometer 50, the characteristics of the movement can be compared by the control circuitry to a predetermined threshold value (e.g., a threshold movement indicative of the aforementioned "bump" or tap movement). If the detected movement is greater than or equal to the threshold value, the NFC circuit 40 can potentially be activated. But, if no movement that is greater than or equal to the threshold value is detected, the NFC circuit 40 is not activated (even if the NFC circuit 40 is within the required proximity of the NFC tag 45 such that NFC communications can potentially be performed). Therefore, in some embodiments this feature operates to enable NFC when the following two conditions are simultaneously met, or are both met within an establish time interval: (i) an acceleration or an acceleration profile that is greater than or equal to a threshold value is detected (indicating, e.g., a tap or other "bump" action between the portable pump 60 and the NFC tag 45), and (ii) the NFC circuit 40 is in proximity with the NFC tag 45 such that communications therebetween using NFC can occur. In some embodiments, the feature provided by the accelerometer 50 can be activated or deactivated based on a user's or clinician's selection of the feature via the configuration parameters of the portable pump 60. In some embodiments, the accelerometer 50 can be used in conjunction with the NFC circuit 40 in other ways so as to include the detection of a movement into the process for activating or completing changes to the portable pump 60 that correspond to the NFC tag 45.

In some embodiments, the portable pump 60 can be configured to respond differently when the acceleration threshold value is detected by the accelerometer 50 as compared to when the acceleration threshold value is not detected. For example, as described previously, in response to the detection of the NFC tag 45 by the NFC circuit 40 the user may be asked to confirm via the user interface 62 whether to initiate a change to the portable pump 60, such as initiating a bolus of insulin. However, if an acceleration that meets or exceeds the established threshold is detected by accelerometer 50, and the NFC tag 45 is simultaneously detected (or detected within a threshold time limit) by the NFC circuit 40, in some cases the portable pump 60 may initiate a bolus without requiring additional user confirmation. Still, in some cases additional user confirmation may nevertheless be required before the bolus is initiated.

Figure 2:
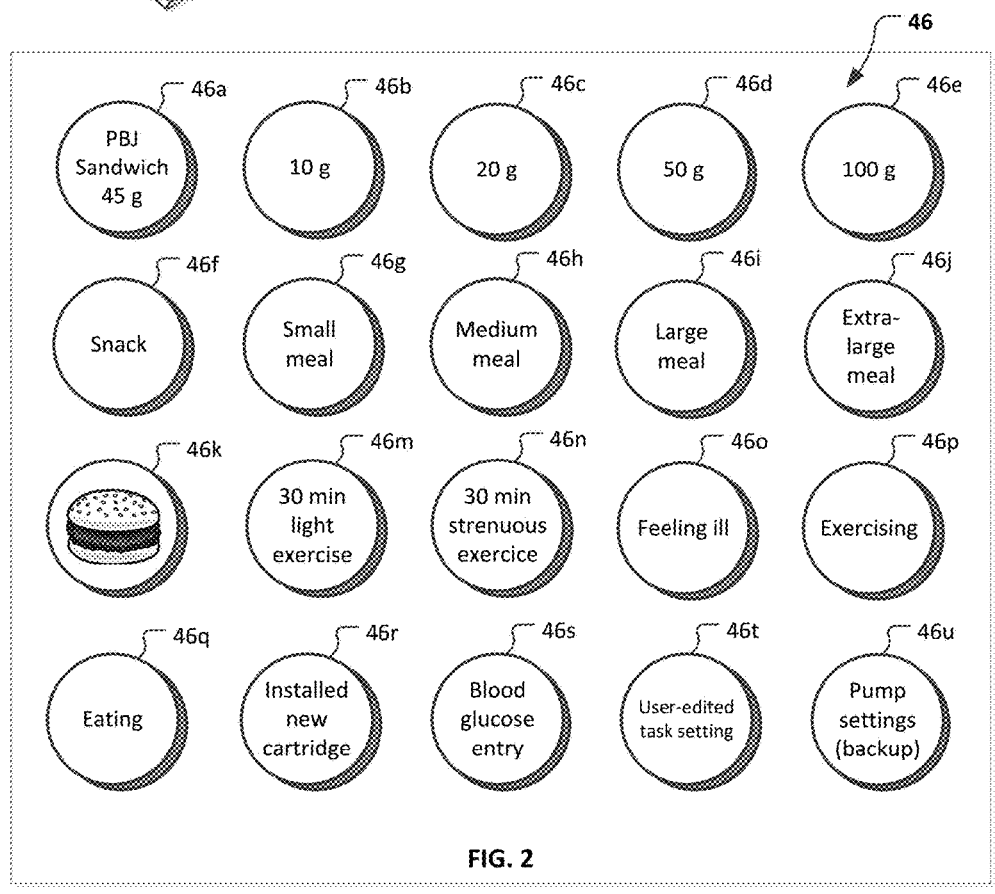
FIG. 2 depicts an assortment of example NFC tags that can be used with the infusion pump systems described herein.

Referring now to FIGS. 1-2, a set of example NFC tags 46 can be employed for communicating with the portable pump 60 as need by the user of the infusion pump system 10. For example, some or all of the set of NFC tags 46 can be selected to correspond with the user's commonly performed tasks associated with using the infusion pump system 10. The NFC tags 46 can be distinctly labeled with text, numbers, graphics, colors, textures, braille, photos, symbols, icons, and the like (and combinations thereof) to assist the user to properly and conveniently distinguish between the various types of NFC tags 46. In some embodiments, the NFC tags 46 can have different physical sizes and shapes, and such sizes and shapes can correspond to an amount of carbohydrates associated with the NFC tags 46. In particular embodiments, an assortment of multiple NFC tags 46 can be included on a sheet of flexible plastic film or paper, in a pocket-sized book, on a key ring, in a container, and in many other convenient storage and handling configurations.

In one example, a parent may pack a lunch for a diabetic child to take to school, and one or more NFC tags 46 corresponding to the particular lunch food can be packed along with the lunch. Or, the NFC tags 46 can be carried by the child (e.g., in a pocket, worn on a necklace or article of clothing). At the school lunchroom, the child can simply tap the child's infusion pump to the NFC tags 46 in order to command the pump to deliver an appropriate bolus dispensation of insulin in correspondence to the food consumed. Thus, as this example shows, using the NFC tags 46 the user can efficiently, accurately, and conveniently initiate commands to the infusion pump system 10 by activating NFC communications between the infusion pump system 10 and the NFC tags 46 (and, optionally, without the need to input a series of menu selections or other more complex user interface actions). In addition, as will be described further, particular NFC tags 46 can be used to receive and store data from the infusion pump system 10.

Some people often eat the same types of foods on a relatively regular basis. A user of the infusion pump system 10 can therefore obtain or make NFC tags that correspond to the food items that the user commonly consumes. For example, the NFC tag 46a (FIG. 2) for a peanut butter and jelly sandwich could be readily used by a user that regularly consumes such sandwich. As described previously, NFC tag 46a can have associated with it (either on the NFC tag 46a, or in the control circuitry of the portable pump 60 in association with a unique identifier of the NFC tag 46a) data such as the grams of carbohydrates of the food represented by the NFC tag 46a. In addition to the grams of carbohydrates, the user's preferred way to deliver a corresponding bolus can be included in the data associated with the NFC tag 46a. For example, the preferred delivery schedule of insulin for the user to counteract the consumption of a peanut butter and jelly sandwich may be 40% of the bolus insulin amount delivered immediately and 60% spread over the next three hours. Of course, a different user may have a different preferred delivery schedule that can be used in correspondence with NFC tags used by the different user. For another type of food item, the preferred delivery schedule of insulin for the user may be other than 40% immediately and 60% spread over the next three hours. For example, for a piece of pie, as represented by the NFC tag 45, the preferred delivery schedule of insulin for the user may be 50% immediately and 50% spread over the next two hours. As such, the data associated with NFC tag 45 can include the corresponding preferred delivery schedule of insulin of 50% immediately and 50% spread over the next two hours.

Still further, other data, in addition to grams of carbohydrates and preferred insulin delivery schedules, can be associated with the NFC tags 46. For example, in some embodiments the fat content, type of fat content, fiber content, protein content, and the like, of the food represented by the NFC tags 46 can be associated with the NFC tags. In some embodiments, such data can be incorporated into a recommended insulin dispensation for the user as calculated by the control circuitry of the portable pump 60. For example, in some instances meals with increased fat can lead to delayed absorption of the carbohydrates, and thus a bolus determined based on other food contents beyond just carbohydrates, (e.g., fat and protein) may be beneficial.

While a user of the infusion pump system 10 may consume certain foods like a peanut butter and jelly sandwich fairly regularly, in some circumstances the user may consume a food item for which the user does not have a dedicated NFC tag 46. In those circumstances, NFC tags 46b, 46c, 46d, and 46e can be used if the user so desires. To use the NFC tags 46b, 46c, 46d, and 46e, the user will estimate the carbohydrate content of the foods that the user has or will soon consume. If, for example, the user will consume food having a carbohydrate content of about 10 grams, the user can activate NFC between the portable pump 60 and the NFC tag 46b (where the NFC tag 46b corresponds to 10 grams of carbohydrates). In response, the portable pump 60 may determine a recommended bolus of insulin and either initiate the dispensation of the bolus or prompt the user to confirm via the user interface 62 the initiation of the recommended bolus of insulin. The NFC tags 46c, 46d, and 46e can be similarly used in situations where about 20, 50, or 100 grams of carbohydrates, respectively, have been or will soon be consumed. Of course, the carbohydrate quantities of 10, 20, 50, and 100 grams associated with NFC tags 46b, 46c, 46d, and 46e are merely illustrative, as NFC tags 46 having any other quantities of carbohydrates (and other data content) can be created and used in accordance with the systems and methods provided herein.

In another example that is relevant to the use of NFC tags 46b, 46c, 46d, and 46e, it may be determined that the user has or will consume food having a carbohydrate content of about 30 grams. In a first example for handling such a scenario, in some embodiments the portable pump 60 can be configured to add together successive NFC tag data entries to input the total carbohydrate quantity desired by the user. For example, to input 30 grams of carbohydrates, the user may first activate NFC between the portable pump 60 and the NFC tag 46b to input 10 grams of carbohydrates. Before confirming a bolus dispensation corresponding to the 10 grams, the user can then activate NFC between the portable pump 60 and the NFC tag 46c to input an additional 20 grams of carbohydrates, for 30 total grams of carbohydrates. In other words, the portable pump 60 can add the first NFC input of 10 grams of carbohydrates and the second NFC input of 20 grams of carbohydrates together to arrive at a total of 30 grams of carbohydrates. The portable pump 60 can then present to the user via the display 65 a prompt that asks the user to confirm the input of 30 grams of carbohydrates to be consumed, and to confirm the acceptance of the associated recommended bolus dispensation of insulin. For example, in the example portable pump 60 provided, the user can confirm the acceptance of such information by activating the button 64c. In other examples, other techniques for confirming acceptance can be used, as described further herein.

While the first example immediately above used NFC tags 46b and 46c to enter a total of 30 grams of carbohydrates into portable pump 60, in a second example technique for entering 30 grams of carbohydrates, the single NFC tag 46b (10 grams of carbohydrates) can be used to activate NCF circuit 40 three times to cause three successive data entries of 10 grams of carbohydrates each. The three successive data entries of 10 grams of carbohydrates each can be added together by portable pump 60 in the manner described above, resulting in a total entry of 30 grams of carbohydrates. The user can then confirm the entry of 30 grams and accept the recommended bolus using the user interface 62. By way of these examples, it should be appreciated that by combining successive data entries using various NFC tags 46, such as NFC tags 46b, 46c, 46d, and 46e, any desired amount of grams of carbohydrates can be entered into portable pump 60 using NFC technology. While in these examples the portable pump 60 was configured to add together successive NFC data entries, in some embodiments the portable pump 60 can alternatively be configured to not add such successive entries together. In some embodiments, the user (or another individual such as a parent or clinician) can selectively configure the portable pump 60 to either add successive entries together or to not add successive entries together.

Still referring to FIGS. 1 and 2, NFC tags 46f, 46g, 46h, 46i, and 46j are examples of NFC tags that can be conveniently used to enter an estimated quantity of carbohydrates (and optionally other nutritional and operational data) in correspondence to an amount of food consumed, or soon to be consumed, by the user. In general, the NFC tags 46f, 46g, 46h, 46i, and 46j can be used as an alternative to counting carbohydrates and entering into the portable pump 60 (via the user interface 62 or via the NFC tags 46b, 46c, 46d, and 46e) the numerical carbohydrate intake quantity to be consumed (e.g., 10, 20, or 30 grams, etc.). As shown, the NFC tags 46f, 46g, 46h, 46i, and 46j can be graduated in relation to an approximate amount of food consumed (e.g., "snack," "small meal," "medium meal," "large meal," and "extra-large meal"). Such approximations may be appropriate for use by some infusion pump system 10 users or in some situations of using the infusion pump system 10. Accordingly, when the user presents the NFC tag 46f (corresponding to a "snack") to portable pump 60 to activate NFC between the NFC tag 46f and the portable pump 60, a lesser quantity of carbohydrates will be input to portable pump 60 in comparison to when the user presents the NFC tag 46i ("large meal") to the portable pump 60. Of course, the NFC tags 46f, 46g, 46h, 46i, and 46j can be configured to correspond to different levels of carbohydrates for different users. For example, a "large meal" for a male may typically include a greater quantity of carbohydrates than a "large meal" for a female. Therefore, in one example a male user of portable pump 60 may configure (program) NFC tag 46i to correspond to 200 grams of carbohydrates, while a female user may configure NFC tag 46i to correspond to 150 grams of carbohydrates. It should be appreciated the quantity of carbohydrates (and other such data) associated with the NFC tags 46f, 46g, 46h, 46i, and 46j can be individualized for the particular user of the infusion pump system 10.

NFC tag 46k is an example of a NFC tag that includes an iconic identifier on a surface of the NFC tag 46k. In this example, an icon of a hamburger is printed on the NFC tag 46k. Using icons, symbols, and other types of non-text identifiers can be advantageous for some users. For example, certain users of the NFC tags 46 may not have fluency in the language printed on the NFC tags 46. Or, a user of the NFC tags 46 may be illiterate, a child, or have poor eyesight. In another example, the NFC tags 46 can include Braille or other raised patterns or shapes for use by blind users or users with limited vision.

NFC tags 46m and 46n are examples of NFC tags that correspond to an exercise activity to be performed by the user of the infusion pump system 10. Diabetic individuals typically experience a blood sugar reduction in response to the performance of exercise. Therefore, to maintain the user's blood sugar level within a target range it can be beneficial to temporarily reduce the user's basal rate to an extent that correlates to the level of physical exertion performed or to be performed. When reducing basal insulin, the appropriate extent of reduction will depend on factors such as intensity, duration, the individual, and mode of exercise. A basal rate can be reduced prior to, during, and after exercise depending on the situation. For example, in response to performing light exercise over a 30 minute period, the user may present NFC tag 46m to the user's portable pump 60. The NFC tag 46m, for example, may be associated with a command for a 50% reduction of the basal insulin dosages over the next 6 hours. In another example, in response to performing 30 minutes of strenuous exercise, the user may present NFC tag 46n to the user's portable pump 60. The NFC tag 46n may, for example, be associated with a command for a 50% reduction of basal insulin over the next 10 hours. Such factors can be individualized for the particular user, and the particular user's NFC tags 46m and 46n can be programmed accordingly. In some embodiments, the NFC tags 46m and 46n can be used in combinations to additively arrive at other levels of exertion or duration in a manner analogous to that described above in reference to NFC tags 46b-e.

NFC tags 46o, 46p, 46q, and 46r are examples of NFC tags that can be used to automate the entry and time-based archival of event occurrences into the portable pump 60. In other words, the NFC tags 46o-46r can be used to add descriptive information to the data that is stored within the portable pump 60. Such labeling of data is also known as data tagging or the creation of metadata. For example, if the user is feeling ill, the user can present the NFC tag 46o to the user's portable pump 60. Upon the activation of NFC between the NFC tag 46o and the NFC circuit 40, a command is executed that causes the portable pump 60 to store metadata identifying that the user feels ill at the time that the NFC was activated. In other examples, when the user is exercising, eating, or has installed a new medicine cartridge, the user can present the NFC tags 46p, 46q, or 46r, respectively, to the user's portable pump 60. Upon the activation of NFC between the NFC tags 46p, 46q, or 46r and the NFC circuit 40, a command is executed that causes the portable pump 60 to store metadata identifying that the user is exercising, eating, or has installed a new medicine cartridge at that time. In another example (not shown in FIG. 2), a NFC tag can be used to indicate when the user has changed the infusion site on the user's body. Accordingly, the presentation of such a NFC tag to the user's portable pump 60 will cause metadata to be stored that identifies that the user changed infusion sites about at the time that NFC was activated between the NFC tag and the NFC circuit 40.

NFC tags 46 can also be used to automatically enter other types of commands to the portable pump 60. NFC tags 46 can thereby reduce the need for using buttons 63a-b and 64a-c of the user interface 62 to shuffle through various menus. One example of a type of command that can be automated is the entry of a blood glucose reading using a NFC tag 46s. For example, the user may periodically measure the user's blood glucose level using a blood glucose meter that analyzes a sample of the user's blood using a test strip. The numerical results provided by such a test can then be entered into the user's portable pump 60 to provide the portable pump 60 with the user's actual current blood glucose level. The NFC tag 46s can be used to "key-up" the portable pump 60 for the entry of the numeric blood glucose level. For example, when the user presents the NFC tag 46s to the portable pump 60 and NFC is established therebetween, a command is executed that causes the portable pump 60 to get ready to receive the blood glucose data with no other preliminary button pushing required. In such fashion, the user can save time and can operate the infusion pump system 10 with greater convenience using the NFC tag 46s. Of course, many other types of commands for the portable pump 60 can be similarly automated using the NFC tags 46.

NFC tag 46t is an example of a "blank" NFC tag that can be programmed or scripted and thereafter used to input a variety of commands to the portable pump 60. In some embodiments, the NFC tag 46t can be programmed by the portable pump 60. In particular embodiments, the NFC tag 46t can be programmed by another device that has NFC functionality (e.g., a smart phone, tablet computer, personal computer, and the like). In some embodiments, the NFC tag 46t can be written to only once, and thereafter the NFC tag 46t becomes a read-only NFC tag. In other embodiments, the NFC tag 46t can be written to, and re-written to, multiple times.

The programmable NFC tag 46t can be utilized in a variety of advantageous ways. For instance, as described above a user of the infusion pump system 10 can program the NFC tag 46t to be associated with data corresponding to a certain type of food that the user consumes (e.g., a large apple having 30 carbs, etc.). In another category of examples, the user can configure the NFC tag 46t to be used to initiate a particular operation by the portable pump 60. For example, when changing an infusion set 70 or a medicine cartridge, the user may first want to pause the portable pump 60. Accordingly, the programmable NFC tag 46t can be programmed to pause the portable pump 60 if the portable pump 60 is in the run mode at the time that NFC is activated between the programmed NFC tag 46t and the portable pump 60. Then, after changing the infusion set 70 or the medicine cartridge, the user may desire to prime the infusion set 70 and begin normal operations of the infusion pump system 70. Therefore, the programmable NFC tag 46t can be programmed to prime and thereafter start the portable pump 60 if the portable pump 60 is in the pause mode at the time that NFC is activated between the programmed NFC tag 46t and the portable pump 60. In accordance with the examples provided above, it can be appreciated that programmable NFC tag 46t provides a versatile and customizable functionality whereby users of infusion pump system 10 can enhance and simplify interactions with the user control interface 62 and operational capabilities of the portable pump 60.

It should be understood from the description herein that a multitude of other beneficial uses for the NFC tags are envisioned for use in combination with a medical infusion pump system. Here, the infusion pump system 70 performs a variety of tasks or receives a various types of user entry associated with operating the infusion pump system 70. Any one of these tasks or types of user entry associated with operating the infusion pump system 70 can be communicated to the control circuitry of the portable pump 60 via the NFC circuit 40 using the corresponding NFC tag. For example, a NFC tag can be used to confirm a user input or pump parameter setting. A NFC tag of this type can be used in conjunction with other NFC tags or input methods to eliminate the need for entering a confirmation using the user interface 62. In another example, a NFC tag can be used to enter a task command to calibrate a glucose sensor. That is, for example, a NFC tag can trigger the portable pump 60 to use the last blood glucose value entered by the user to calibrate a continuous glucose monitor that is in communication with the infusion pump system 70. In another example, in some circumstances, such as when the infusion pump system 70 is used by a child or when the infusion pump system 70 is used during sports activities, it may be desirable to temporarily deactivate the functionality of the buttons 63*a*, 63*b*, 64*a*, 64*b*, and 64*c* of the user interface 62. In such circumstances, NFC tags can be used to lock, and subsequently unlock, the buttons 63*a*, 63*b*, 64*a*, 64*b*, and 64*c* of the user interface 62. In still another example, a NFC tag can be used to stop or pause the portable pump 60, such as when the user has disconnected the portable pump 60 from the infusion set 70 to bathe. NFC tags can also be used to enter a task or user command to change to a different basal pattern. Such changes may be beneficial during weekends versus weekdays, during menses versus the rest of the month, and so on. It should be understood that the example uses for NFC tags provided herein are non-limiting, and that other uses for the NFC tags are also envisioned.

NFC tag 46*u* is an example of another use for a "blank" NFC tag that can be written to. In this example, the NFC tag 46*u* is used to store the user configuration settings for the user's portable pump 60. Using the NFC tag 46*u* in this manner can provide a way to create a back-up copy of the user's configuration settings. Having a back-up copy of the user's configuration settings can be advantageous in a variety of circumstances. For example, if the user's portable pump 60 is damaged such that a repair is necessitated, the NFC tag 46*u* containing the user's settings can be used to conveniently reprogram the repaired portable pump 60 by presenting the NFC tag 46*u* to the repaired portable pump 60. Or, if the user's portable pump 60 is damaged beyond repair, the user's settings can be conveniently uploaded to a replacement portable pump 60 by presenting the NFC tag 46*u* to the replacement portable pump 60. Or, if the user desires different settings for different situations, such NFC tags comprising user settings can conveniently be used to change the settings.

Figure 3:
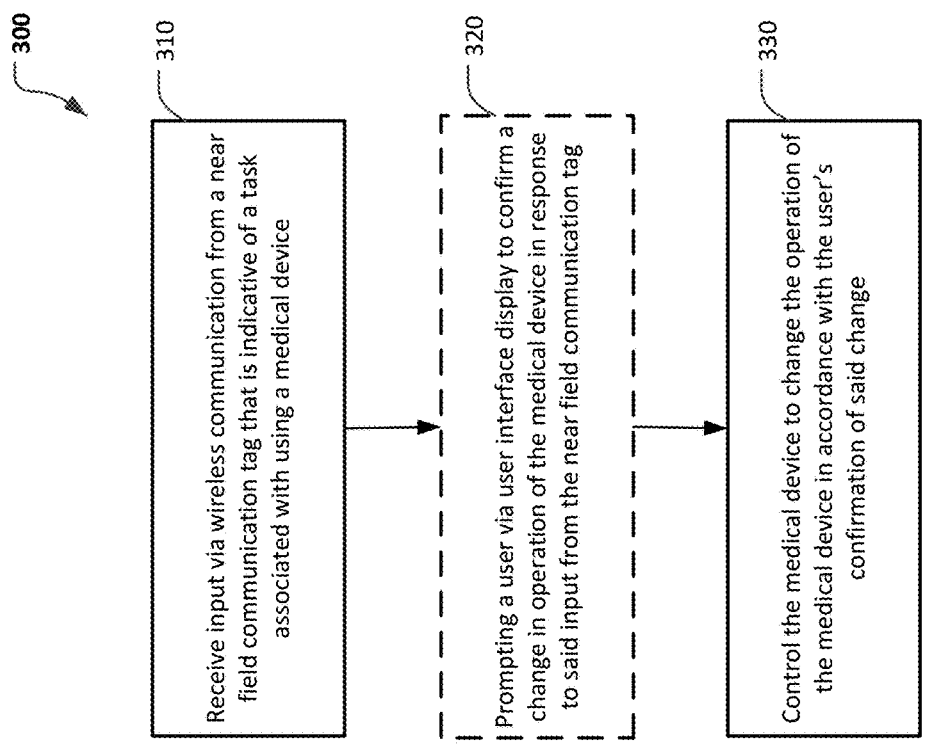
FIG. 3 is a flowchart describing a process of using an infusion pump system equipped with NFC capabilities in accordance with some embodiments.

Referring now to FIG. 3, the control circuitry of a medical device (e.g., a portable infusion pump in this embodiment) that includes NFC equipment can implement a process 300 of receiving commands from a NFC tag, and controlling the medical device in accordance with the commands. Such a process 300, for example, can be implemented by the control circuitry housed in the portable pump 60 of the infusion pump system 10 (FIG. 1), and other embodiments of infusion pump systems provided herein (e.g., FIGS. 4, 5, 6, and 7).

In operation 310, the control circuitry of a medical device can receive input via wireless communication from a NFC tag. The input can be indicative of a task associated with using the medical device. A medical device that can perform operation 310 is exemplified in FIG. 1, where the infusion pump system 10 includes a NFC circuit 40 that is in electrical communication with the control circuitry of the infusion pump system 10. As explained, the NFC circuitry 40 can function to send and receive communications from the NFC tag 45 when NFC is activated by placing the NFC tag 45 within the requisite proximity with the portable pump 60 such that NFC communications are activated.

In some embodiments, NFC tags can be scripted with executable code that can be transferred to the medical device's control circuitry via the NFC circuit in communication with the control circuitry. In those embodiments, the control circuitry can execute the code as received from the NFC tag. In other embodiments, the NFC tag can communicate a unique identifier, such as a serial number, to the control circuitry via the NFC circuit. In response to the receipt of such a unique identifier by the control circuitry, the control circuitry can execute certain coded operations that are associated with the particular unique identifier received.

An example of operation 310 is provided in FIG. 1, where the NFC tag 45 is presented to the NFC circuit 40 of the portable pump 60. In response, the control circuitry of the portable pump 60 executed commands indicative of an entry by the user of an intent to initiate a bolus dispensation to counteract the consumption of 60 grams of carbohydrates.

In operation 320, the control circuitry optionally provides a prompt via the user interface display to confirm a change in operation of the medical device in response to said input from the near field communication tag. Such a prompt may be advantageously used to confirm the user's intent to change the operation of the medical device before the control circuitry actually implements the change.

An example of operation 320 is provided in FIG. 1, where the control circuitry of the portable pump 60 generated the illustrated textual prompt on the display 65. The prompt provides a description of the potential change in operation ("Consume 60 g of carbs? Press enter to initiate a bolus of 4.0 U."). By pressing button 64*c* the user can confirm the user's intent to implement a change in the operation of the infusion pump system 10. Alternatively or additionally, other techniques can be used to confirm the user's intent to change the operation of the medical device before the control circuitry actually implements the change. For example, in some embodiments the user can be required to present the same NFC tag to the NFC circuit multiple times within a limited period of time (e.g., two quick taps, three taps within a period of two second, or the like) to confirm the user's intent. In particular embodiments, the user can be required to make contact (e.g., by tapping or otherwise bumping, or the like) between the pump device and the NFC tag, and such contact can be considered to be sufficient user confirmation. In such embodiments, one or more accelerometers in the pump device may be used to detect the requisite contact(s). In other embodiments, some types of tasks entered using a NFC tag require user confirmation while other types of tasks entered using a NFC tag do not require user confirmation. In still other embodiments, a particular task that is entered using a NFC tag will require a user confirmation in some circumstances, but not in other circumstances. An infusion pump system may be configurable to select between the use of these types of alternative techniques for user confirmation. In some embodiments, such various alternatives can be combined for use with various types of tasks associated with a single pump system. In particular embodiments, the infusion pump system can be configured to not require user confirmation for some, or all, tasks and commands entered using NFC tags.

In operation 330, after receiving confirmation from the user to implement the change associated with the input from the NFC tag, the control circuitry can control the medical device to change the operation of the medical device in accordance with the user's confirmation of the change. Again in regard to the example of FIG. 1, when the user confirms by pressing button 64*c* the change to the infusion pump system 10 related to the user's consumption of 60 grams of carbohydrates, the control circuitry can thereafter control the portable pump 60 to deliver the corresponding bolus dispensation of insulin.

Figure 4:
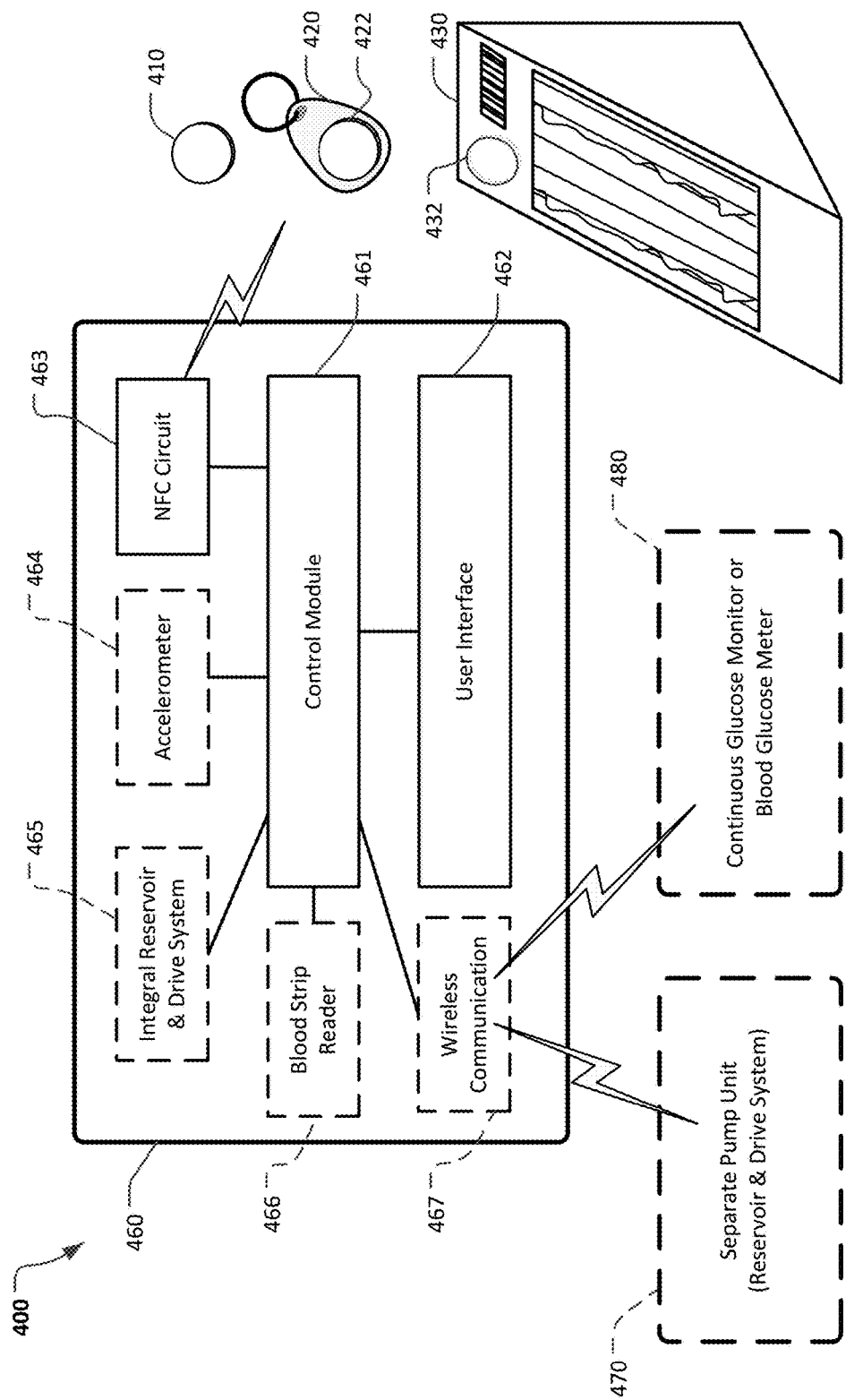
FIG. 4 is a schematic diagram of an infusion pump system with NFC capabilities in accordance with some embodiments.

Now referring to FIG. 4, a schematically represented example portable infusion pump system 400 can include a pump controller device 460 that is equipped with a NFC circuit 463 for providing NFC capabilities. The NFC circuit 463 can be used by the infusion pump system 400 to communicate with example NFC tags 410, 422, and 432. Certain items of the infusion pump system 400 are shown with dashed lines to indicate that they are optional or alternative items, as explained below.

The pump controller device 460 includes a control module 461 that can be made up of one or more components. In this embodiment, the control module 461 is configured to communicate control or power signals to the other components of the infusion pump system 400, and to receive inputs and signals therefrom. In some embodiments, the control circuitry can include a main processor board that is in communication with a power supply board. The control circuitry can include at least one processor that coordinates the electrical communication to and from the control module 461 and other components of the pump system 400. For example, the user interface 462 of the pump controller device 460 can include input components and output components that are electrically connected to the control circuitry of the control module 461. In some embodiments, the control module 461 can receive input commands from a user's button selections (e.g., buttons as shown in FIG. 1, 5, 6, or 7), and thereby cause the display device of the user interface 462 to output a number of menus or program screens that show particular settings and data (e.g., review data that shows the medicine dispensing rate, the total amount of medicine dispensed in a given time period, the amount of medicine scheduled to be dispensed at a particular time or date, the approximate amount of medicine remaining the cartridge, the amount of battery life remaining, or the like).

The processor of the control module 461 can be arranged on a main processor circuit board of the control module 461 along with a number of other electrical components such as computer-readable memory devices. The control circuitry can be programmable in that the user or a clinician may provide one or more instructions to adjust a number of settings for the operation of the infusion pump system 400. Such settings may be stored in the memory devices of the control module 461. Furthermore, the control module 461 may include one or more dedicated memory devices that store executable software instructions for the processor. The control module 461 may include other components, such as sensors, that are electrically connected to the main processor board. A rechargeable battery pack (not shown) may provide electrical energy to the control module 461, and to other components of the pump controller device 460 (e.g., user interface 462, NFC circuit 463, and others).

The user interface 462 of the pump controller device 460 permits a user to monitor and control the operation of the pump controller device 460. For example, the user interface 462 can include a display device having an active area that outputs information to a user, and buttons (e.g., actuatable buttons as shown in FIG. 1, 5, 6, or 7 or touchscreen buttons defined on the display device) that the user can use to provide input. The display device can be used to communicate a number of settings or menu options for the infusion pump system 400. The display may include an active area in which numerals, text, symbols, images, or a combination thereof can be displayed (refer, for example, to FIG. 1). For example, the user may press one or more buttons to shuffle through a number of menus or program screens that show particular settings and data (e.g., review data that shows the medicine dispensing rate, the total amount of medicine dispensed in a given time period, the amount of medicine scheduled to be dispensed at a particular time or date, the approximate amount of medicine remaining in the cartridge, or the like). In some embodiments, the user can adjust the settings or otherwise program the control module 461 via the user interface 462. For example, in embodiments of the infusion pump system 400 configured to dispense insulin, the user may press one or more of the buttons of the user interface 462 to change the dispensation rate of insulin or to request that a bolus of insulin be dispensed immediately or at a scheduled, later time.

The pump controller device 460 also includes the NFC circuit 463 in electrical communication with the control module 461, such that power and signal data can be transferred between the NFC circuit 463 and the control module 461. The NFC circuit 463 in this embodiment includes a NFC transceiver circuit that is coupled to a loop inductor (e.g., coil) that serves as an antenna for wirelessly communicating with external NFC tags (e.g., NFC tags 410, 422, and 432). The NFC circuit 463 can act as an interface to facilitate the transfer of data between the example NFC tags 410, 422, and 432 and the control module 461 using NFC protocols. The coil of the NFC circuit 463 inductively supplies electrical power to the NFC tags 410, 422, and 432 by way of secondary coils located in the NFC tags 410, 422, and 432 themselves. The respective coils of the NFC circuit 463 and the NFC tags 410, 422, and 432 can also wirelessly exchange two-way data transmissions using the same inductive coupling between the coils.

The example NFC tags 410, 422, and 432 depict some additional advantageous ways of configuring NFC tags to be used in conjunction with the infusion pump system 400. In general, NFC tags 410, 422, and 432 include a coil and a microchip. The NFC tags 410, 422, and 432 act as passive listening devices. But when the NFC circuit 463 is located in the requisite proximity to the NFC tags 410, 422, or 432, the coil of the NFC tags 410, 422, or 432 inductively couples with a coil of the NFC circuit 463. When the coils are inductively coupled, electrical power is supplied to the NFC tags 410, 422, or 432 and data can be exchanged between the NFC tags 410, 422, or 432 and the NFC circuit 463. In some embodiments, about a kilobyte of data or more can be stored in the NFC tags 410, 422, and 432 and transferred to the control module 461 via the NFC circuit 463.

The NFC tag 410 is an example of a compact and versatile NFC tag. In some embodiments, NFC tag 410 is about the size of a quarter and is flexible. NFC tag 410 can have an adhesive coating on one surface. In some embodiments, the NFC tag 410 can be incorporated into configurations such as pendants, tiles, chips, stickers, and the like.

The NFC tag 422 is an example of a NFC tag that has been conveniently incorporated onto a keychain 420. In one example use of such a configuration, the keychain 420 can be attached to a gym bag and the NFC tag 422 can be programmed like the NFC tags 46m or 46n of FIG. 2, that indicate that the user is going to perform 30 minutes of light or strenuous exercise respectively. Then, in conjunction with the user's exercise, the user can simply present the NFC tag 422 on the keychain 420 to the user's pump controller device 460 (e.g., tapping the pump controller device 460 against the tag 432 or in proximity to the tag 432) to enter a command corresponding to the performance of the exercise.

The NFC tag 432 in an example of a NFC tag that has been conveniently incorporated onto a food package 430. In this example, the food package 430 is a sandwich container like those commonly available from a vending machine or convenience store. As shown, the NFC tag 432 can be adhered to or otherwise incorporated directly on the exterior of the food package 430. The NFC tag 432 can be preprogrammed with data corresponding to the contents of the food package 430. For example, the NFC tag 432 can be programmed with the number of grams of carbohydrates in the sandwich contained in the food package 430. The user of the infusion pump system 400 can conveniently present the NFC tag 432 to the NFC circuit 463 of the pump controller device 460 (e.g., tapping the pump controller device 460 against the tag 432 or in proximity to the tag 432) to enter a command corresponding to the consumption of the sandwich inside of the food package 430.

The pump controller device 460 can also optionally include an accelerometer 464 in electrical communication with the control module 461. In some embodiments, more than one accelerometer 464 can be optionally included. Embodiments of the pump controller device 460 that include the optional accelerometer 464 can utilize the functionality of the accelerometer 464 in conjunction with the NFC circuit 463. That is, the accelerometer 464 can operate in conjunction with the control module 461 and the NFC circuit 463 to supplement the criteria for activating or completing communications between the NFC circuit 463 and the NFC tags 410, 422, or 432. In other words, while in some embodiments communications between the NFC circuit 463 and the NFC tags 410, 422, or 432 are activated solely based on the proximity therebetween, in other embodiments a threshold acceleration, as determined by the accelerometer 464, must also be detected. An objective for including this feature can be to more clearly ascertain that the user intends to activate NFC when a NFC tag 410, 422, or 432 is within the required proximity with the NFC circuit 464. That is, for example, by requiring the user to tap the pump assembly 460 and the NFC tag 410, 422, or 432 together, the user's intentions for activating NFC may be ascertained with a greater level of confidence.

This optional feature using the accelerometer 464 can function as follows. When motion of the pump controller device 460 is detected by accelerometer 464, a characteristic value of the detected motion can be compared by the control module 461 to a predetermined threshold movement value. If the characteristic value of the detected movement is greater than the threshold value, the NFC circuit 463 can potentially be activated. But, if the characteristic value of the detected movement is not greater than the threshold value, the NFC circuit 463 is not activated (even if the NFC circuit 463 is within the required proximity of the NFC tags 410, 422, or 432 such that NFC communications can be performed). Therefore, in some embodiments this feature operates to enable NFC when the following two conditions are simultaneously met, or are both met within an establish time interval: (i) a characteristic value of the detected movement (e.g., acceleration value) that is greater than a threshold value is detected (indicating, for example, a tap), and (ii) the NFC circuit 463 is in proximity with the NFC tags 410, 422, or 432 such that communications therebetween using NFC can occur.

Still referring to FIG. 4, in some embodiments the pump controller device 460 may also serve as the pump unit for the infusion pump system 400, thereby dispensing medicine from the same housing that contains the control module 461 and other components. In those particular embodiments, the pump controller device 460 can be optionally equipped with an integral medicine reservoir and drive system 465 in electrical communication with the control module 461. For example, the portable pump 60 depicted in the embodiment of FIG. 1 is an example of this type of configuration. Such embodiments of the portable infusion pump system 400 can employ a reusable pump apparatus (rather than a disposable pump device as will be described below, for example, in connection with FIG. 5). Therefore, in those embodiments, the infusion pump system 400 may optionally serve as a reusable device that houses the control module 461 and the integral reservoir and pump drive system 465 within a single housing construct. In those circumstances, the pump controller device 460 can be adapted to receive a medicine cartridge in the form of a carpule that is preloaded with insulin or another medicine. The pump drive system 465 can act upon the fluid cartridge to controllably dispense medicine through an infusion set and into the user's tissue or vasculature. In this embodiment, the user can wear the pump controller device 460 on the user's skin under clothing or in the user's pocket while receiving the medicine dispensed through the infusion set. In some embodiments of the pump controller device 460 that include the optional integral reservoir and drive system 465, a refillable medicine reservoir can be incorporated in the pump controller device 460 as an alternative to a medicine cartridge.

Still referring to FIG. 4, as an alternative to the integral medicine reservoir and drive system 465, the infusion pump system 400 can include a separate pump device 470 (including a reservoir and a drive system) that is in electrical communication with the pump controller device 460. In these embodiments, the separate pump device 470 can be configured as a disposable and non-reusable pump component while the controller device 460 is configured to be reused with a series of the pump devices 470. In the depicted embodiment shown in FIG. 4, wireless communications are used between the separate pump device 470 and the pump controller device 460, using a wireless communication module 476 in the pump controller device 460. The wireless communications of the wireless communication module 476 can utilize any of a variety of wireless communication technologies that have a greater maximum working range than the aforementioned NFC equipment. For example the wireless communication module 476 can employ Bluetooth, RF (radio frequency), infrared, ultrasonic, electromagnetic induction, and the like, and combinations thereof. Optionally, in some embodiments, the wireless communications of the wireless communication module 476 can utilize NFC equipment. Alternatively, a releasable electrical connection can be used between the separate pump device 470 and the pump controller device 460 so as to provide hardwired electrical communication between the control module 461 of the controller device 460 and the drive system of the pump device 470. One such embodiment of a separate pump device 470 that is removably attachable with the controller device 460 separate pump device 470 is depicted, for example, in FIG. 5 (as described below).

In brief, in embodiments of the infusion pump system 400 that include the separate pump device 470, the pump controller device 460 may be configured as a reusable component that provides electronics and a user interface to control the operation of the infusion pump system 400, and the separate pump device 470 can be a disposable component that is discarded after a single use. For example, the separate pump device 470 can be a "one time use" component that is thrown away after the fluid cartridge therein is exhausted. Thereafter, the user can wirelessly connect or removably mount a new separate pump device 470 to the reusable pump controller device 460 for the dispensation of a new supply of medicine from the new pump device 470. Accordingly, the user is permitted to reuse the pump controller device 460 (which may include complex or valuable electronics) while disposing of the relatively low-cost separate pump device 470 after each use. Such an infusion pump system 400 can provide enhanced user safety as a new separate pump device 470 is employed with each new fluid cartridge.

Still referring to FIG. 4, the pump controller device 460 can also optionally include an integral blood strip reader 466 mounted therein and being in electrical communication with the control module 461. In such embodiments of the pump controller device 460, test strips (e.g., blood test strips) containing a sample of the user's blood can be inserted into the blood strip reader 466 portion of the pump controller device 460, to be tested for characteristics of the user's blood. The results of the analysis can be used to affect the dosage or schedule of medicine dispensations from the pump controller device 460 to the user as determined by the control module 461. As an alternative to or in addition to the internal blood strip reader 466 housed in the pump controller device 460, the pump controller device 460 can be configured to communicate with an external blood glucose detection device 480, such as a continuous glucose monitor or a handheld blood glucose meter. For example, the test strips (e.g., glucose test strips) containing a sample of the user's blood can be inserted into external handheld blood glucose meter 480, which then analyzes the characteristics of the user's blood and communicates the information (via a wired or wireless connection) to the pump controller device 460. In other embodiments, the user interface 462 of the pump controller device 460 can be employed by the user to manually enter the user's blood glucose information as reported on a screen of a handheld blood glucose meter 480. In still other embodiments, the infusion pump system 400 can include a continuous glucose monitor 480 (as an alternative to or in addition to the internally housed blood strip reader 466) that can continuously monitor characteristics of the user's blood and communicate the information (via a wired or wireless connection) to the pump controller device 460. One example of this configuration is described below in connection with FIG. 6.

Figure 5:
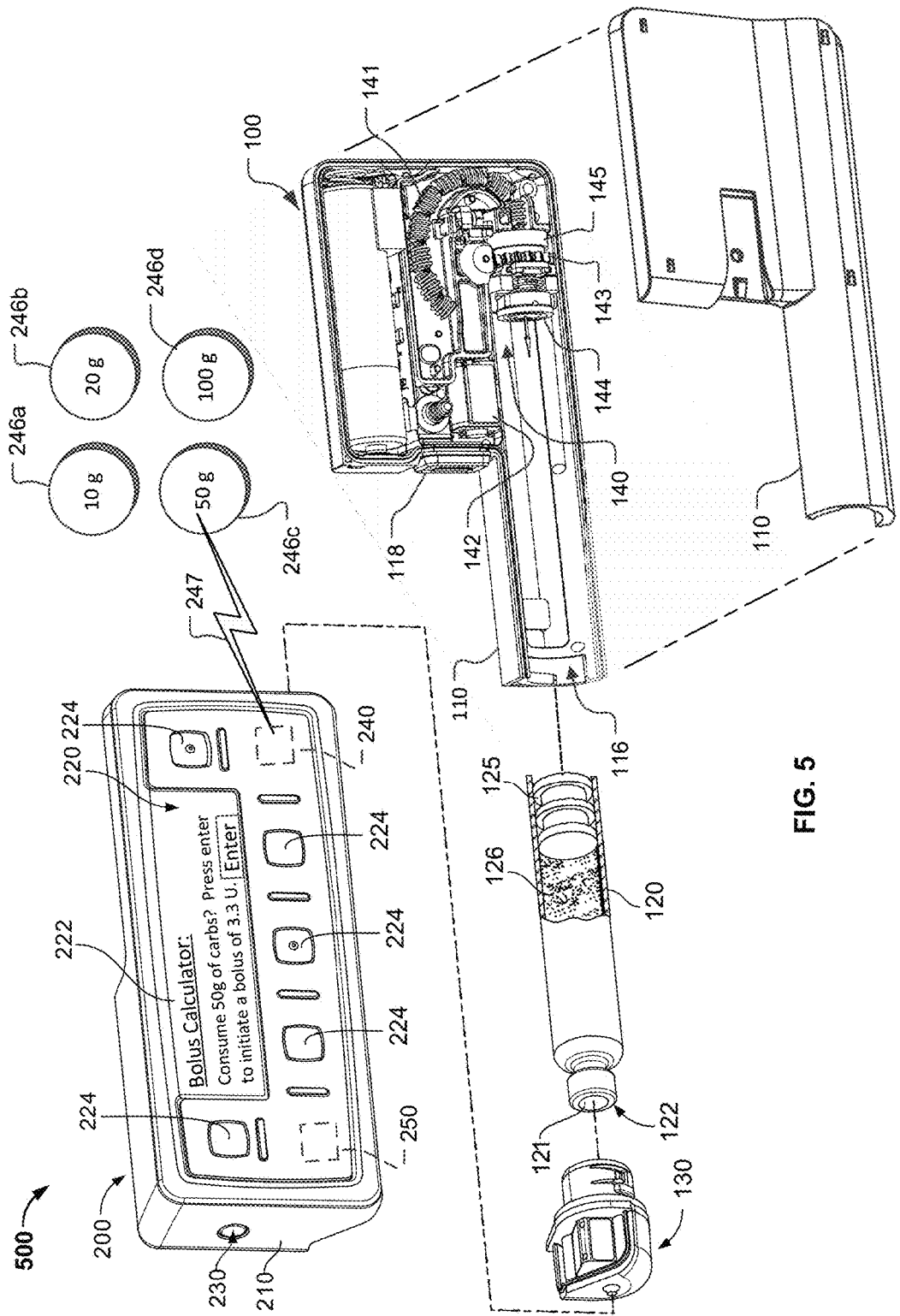
FIG. 5 is an exploded perspective view of another infusion pump system with NFC capabilities in accordance with some embodiments.

Referring now to FIG. 5, some embodiments an infusion pump system 500 equipped with NFC capabilities can include a removable pump device 100 (shown in an exploded view) and a controller device 200 that communicates with the pump device 100. The pump device 100 in this embodiment includes a housing structure 110 that defines a cavity 116 in which a fluid cartridge 120 can be received. The pump device 100 can also include a cap device 130 to retain the fluid cartridge 120 in the cavity 116 of the housing structure 110. The pump device 100 can include a drive system 140 that advances a plunger 125 in the fluid cartridge 120 so as to dispense fluid 126 therefrom.

In some embodiments, the controller device 200 communicates with the pump device 100 to control the operation of the drive system 140. When the controller device 200, the pump device 100 (including the cap device 130), and the fluid cartridge 120 are assembled together, the user can (in some embodiments) conveniently wear the infusion pump system 500 on the user's skin under clothing, in a pouch clipped at the waist (e.g., similar to a cell phone pouch), or in the user's pocket while receiving the fluid dispensed from the pump device 100. Optionally, the controller device 200 may be configured as a reusable component that provides electronics and a user interface to control the operation of the pump device 100. In such circumstances, the pump device 100 can be a disposable component that is disposed of after a single use. For example, the pump device 100 can be a "one time use" component that is thrown away after the fluid cartridge 120 therein is exhausted. Thereafter, the user can removably attach a new pump device 100 (having a new medicine cartridge 120) to the reusable controller device 200 for the dispensation of fluid from a new fluid cartridge 120. Accordingly, the user is permitted to reuse the controller device 200 (which may include complex or valuable electronics, as well as a rechargeable battery) while disposing of the relatively low-cost pump device 100 after each use. Such a pump system 500 can provide enhanced user safety as a new pump device 100 (and drive system therein) is employed with each new fluid cartridge 120.

Briefly, in use, the pump device 100 is configured to removably attach to the controller device 200 in a manner that provides a secure fitting, an overall compact size, and a reliable electrical connection that can be resistant to water migration. For example, the controller device 200 can include a housing 210 having a number of features that mate with complementary features of the pump housing 110. In such circumstances, the controller device 200 can removably attach with the pump device 100 in a generally side-by-side configuration. The compact size permits the infusion pump system 500 to be discrete and portable. Moreover, at least one of the pump device 100 or the controller device 200 can include a release member that facilitates an easy-to-use detachment and replacement process.

As shown in FIG. 5, the pump device 100 can include an electrical connector 118 (e.g., having conductive pads, pins, and the like) that is exposed to the controller device 200 and that mates with a complementary electrical connector (not shown) on the adjacent face of the controller device 200. The electrical connection between the pump device 100 and the controller device 200 provides the electrical communication between the control circuitry housed in the controller device 200 and at least a portion of the drive system 140 or other components of the pump device 100. For example, in some embodiments, the electrical connection between the pump device 100 and the controller device 200 can permit the transmission of electrical control signals to the pump device 100 and the reception of feedback signals (e.g., sensor signals) from particular components within the pump device 100. The electrical connection between the pump device 100 and the controller device 200 may similarly facilitate transmission of one or more power signals for sharing electrical power therebetween.

The pump device 100 may include a drive system 140 that is controlled by the removable controller device 200. Accordingly, the drive system 140 can accurately and incrementally dispense fluid from the pump device 100 in a controlled manner. The drive system 140 may include a flexible piston rod 141 that is incrementally advanced toward the medicine cartridge 120 so as to dispense the medicine from the pump device 100. At least a portion of the drive system 140 is mounted, in this embodiment, to the pump housing 110. In some embodiments, the drive system 140 may include a number of components, such as an electrically powered actuator (e.g., reversible motor 142 or the like), a drive wheel 143, a bearing 145, the flexible piston rod 141, and a plunger engagement device 144. In this embodiment, the reversible motor 142 drives a gear system to cause the rotation of the drive wheel 143 that is coupled with the bearing 145. The drive wheel 143 may include a central aperture with an internal thread pattern, which mates with an external thread pattern on the flexible piston rod 141. The interface of the threaded portions of the drive wheel 143 and flexible piston rod 141 may be used to transmit force from the drive wheel to the piston rod 141. Accordingly, in the embodiment of FIG. 5, the drive wheel 143 is the driver while the flexible piston rod 141 is the driven member. The rotation of the drive wheel 143 can drive the flexible piston rod 141 forward in a linear longitudinal direction to cause the plunger engagement device 144 to nudge the plunger 125 within the fluid cartridge 120 so as to dispense fluid 126 therefrom.

Still referring to FIG. 5, the controller device 200 can include a user interface 220 that permits a user to monitor and control the operation of the pump device 100. In some embodiments, the user interface 220 can include a display device 222 and one or more user-selectable buttons (e.g., several buttons 224 are shown in the embodiment of FIG. 5). The display device 222 can include an active area in which numerals, text, symbols, images, or a combination thereof can be displayed. For example, the display device 222 can be used to communicate a number of settings or menu options for the infusion pump system 500. In this embodiment, the user may press one or more of the buttons 224 to shuffle through a number of menus or program screens that show particular settings and data (e.g., review data that shows the medicine dispensing rate, the total amount of medicine dispensed in a given time period, the amount of medicine scheduled to be dispensed at a particular time or date, the approximate amount of medicine remaining in the cartridge 120, or the like). In some embodiments, the user can adjust the settings or otherwise program the controller device 200 by pressing one or more buttons 224 of the user interface 220. For example, in embodiments of the infusion pump system 500 configured to dispense insulin, the user may press one or more of the buttons 224 to change the dispensation rate of insulin or to request that a bolus of insulin be dispensed immediately or at a scheduled, later time. In some implementations, the display device 222 may also be used to communicate information regarding remaining battery life.

The controller device 200 can also be equipped with an inspection light device 230. The inspection light device 230 can provide the user with a tool to illuminate and inspect a targeted location. For example, the inspection light device 230 can be directed at the infusion site on the user's skin to verify that the infusion set is properly embedded, or the inspection light device 230 can be directed at the pump device 100 to illuminate the cavity 116 or other areas. The inspection light device 230 can also be used to notify the user to an alert condition of the pump system 500. An activation of the inspection light device 230 can thereby provide a visual notification (as an alternative to, or in addition to, the visual notification provided on the display device 222) to the user that attention to the infusion pump system 500 is warranted.

The control device 200 of the system 500 also includes a NFC circuit 240. The NFC circuit 240 can wirelessly communicate with external NFC tags, such as example NFC tags 246a, 246b, 246c, and 246d. As described previously, such wireless communications using NFC technology can enhance and simplify user interactions with the infusion pump system 500. For instance, using NFC, the need for user activation of buttons 224 for shuffling through menus may be reduced in some circumstances. FIG. 5 depicts an example scenario to illustrate this principle. In this example scenario, the user of infusion pump system 500 has consumed, or will soon consume, about 50 grams of carbohydrates. As such, the user desires to schedule or initiate a corresponding bolus dispensation of insulin to counteract the effects of the intake of 50 grams of carbohydrates. The bolus dispensation of insulin is intended to cause the user's blood glucose level to remain within a target range. To schedule or initiate the desired bolus dispensation, the user first positions the controller device 200 containing the NFC circuit 240 in close proximity with the NFC tag 246c (which is programmed to correspond to 50 grams of carbohydrates). Wireless NFC communications can thereby be established between the NFC circuit 240 and the NFC tag 246c (as signified by wireless communication symbol 247). In some embodiments, the user is provided with a notification that NFC communications have been established. The notification can be visual, audible, tactile, and a combination thereof. In response to the communication from the NFC tag 246c to the controller device 200, the controller device 200 provides a prompt to the user on the display device 222. In this example, the prompt on the display device 222 requests the user to confirm that the user desires to receive a 3.3 Unit dispensation of insulin because of the intake of 50 grams of carbohydrates. To confirm the dispensation of the suggested bolus amount, the user can simply press the button 224 directly below the word "Enter." By this example, it can be appreciated that the incorporation of NFC technology in the infusion pump system 500 can enhance and simplify user interactions with the infusion pump system 500, because to initiate an appropriate bolus dosage of insulin the user simply had to present a NFC tag 246c to the NFC circuit 240 and then press button 224 in response to the prompt on the display device 222.

Optionally, the control device 200 can further include at least one accelerometer 250. In some embodiments, the accelerometer 250 can be used as a criteria to activate or complete the NFC communications when a characteristic value of a detected movement of the controller device 200 is at or above the threshold level, as previously described above in connection with FIGS. 1 and 4. In such circumstances, the control circuitry housed in the controller device 200 can be configured to determine when the controller housing 210 is "bumped" against one of the NFC tags 246a-d so as to activate the NFC transmission via the NFC circuit 240.

Figure 6:
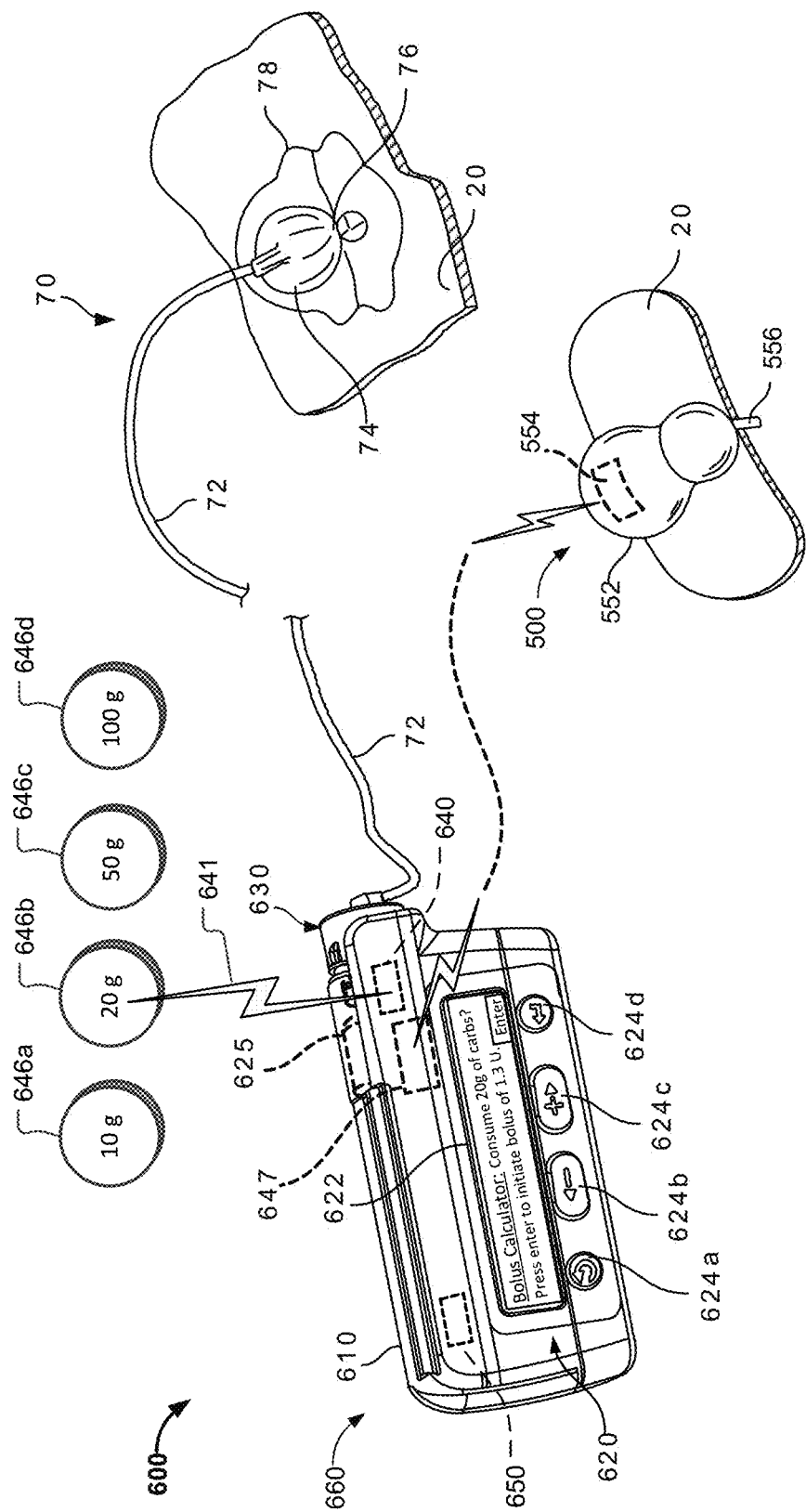
FIG. 6 is a perspective view of another infusion pump system with NFC capabilities in accordance with some embodiments.

Referring now to FIG. 6, some embodiments of an infusion pump system 600 configured to communicate with NFC tags can also be configured to wirelessly communicate with a continuous glucose monitor device 500. For example, in this embodiment, the system 600 can include a pump assembly 660 used to supply insulin or another medication to a user via, for example, an infusion set 70. The glucose monitoring device 500 communicates with the pump assembly 660 for the purpose of supplying data indicative of a user's blood glucose level to a control circuitry included in the pump assembly 660. The infusion pump system 600 can utilize the data indicative of a user's blood glucose level in the calculation of a bolus dosage.

In this embodiment, the pump assembly 660 includes a housing structure 610 that defines a cavity in which a fluid cartridge 625 can be received. The pump assembly 660 also includes a cap device 630 to retain the fluid cartridge 625 in the cavity of the housing structure 610. The pump assembly 660 includes a drive system (e.g., described in more detail in connection with FIG. 5) that advances a plunger in the fluid cartridge 625 so as to dispense fluid therefrom. In some embodiments, the dispensed fluid exits the fluid cartridge 625, passes through a flexible tube 72 of the infusion set 70 to a cannula housing 74. The dispensed fluid can enter through the skin 20 via a cannula 76 attached to the underside of the cannula housing 74.

Still referring to FIG. 6, the glucose monitoring device 500 can include a housing 552, a wireless communication device 554, and a sensor shaft 556. The wireless communication device 554 can be contained within the housing 552 and the sensor shaft 556 can extend outward from the housing 552. In use, the sensor shaft 556 can penetrate the skin 20 of a user to make measurements indicative of characteristics of the user's blood (e.g., the user's blood glucose level or the like). In response to the measurements made by the sensor shaft 556, the glucose monitoring device 500 can employ the wireless communication device 554 to transmit data to the control circuitry of the pump assembly 660.

In some embodiments, the monitoring device 500 may include a circuit that permits sensor signals (e.g., data from the sensor shaft 556) to be communicated to the communication device 554. The communication device 554 can transfer the collected data to the pump assembly 660 (e.g., by wireless communication to a communication device 647 arranged in the pump assembly 660). In some embodiments, the monitoring device 500 can employ other methods of obtaining information indicative of a user's blood characteristics and transferring that information to the infusion pump assembly 660. For example, an alternative monitoring device may employ a micropore system in which a laser porator creates tiny holes in the uppermost layer of a user's skin, through which interstitial glucose is measured using a patch. Alternatively, the monitoring device can use iontophoretic methods to non-invasively extract interstitial glucose for measurement. In other examples, the monitoring device can include non-invasive detection systems that employ near IR, ultrasound or spectroscopy, and particular embodiments of glucose-sensing contact lenses. Invasive methods involving optical means of measuring glucose could also be added. In yet another example, the monitoring device can include an optical detection instrument that is inserted through the skin for measuring the user's glucose level.

Furthermore, it should be understood that in some embodiments, the monitoring device 500 can be in communication with the pump assembly 660 via a wired connection. In other embodiments of the pump system 600, test strips (e.g., blood test strips) containing a sample of the user's blood can be inserted into a strip reader portion of the pump assembly 660 to be tested for characteristics of the user's blood. Alternatively, the test strips (e.g., glucose test strips) containing a sample of the user's blood can be inserted into a glucose meter device (not shown in FIG. 6), which then analyzes the characteristics of the user's blood and communicates the information (via a wired or wireless connection) to the pump assembly 660. In still other embodiments, characteristics of the user's blood glucose information can be entered directly into the pump assembly 660 via a user interface 620 on the pump assembly 660.

Still referring to FIG. 6, the pump assembly 660 includes the user interface 620 that permits a user to monitor the operation of the pump assembly 660. In some embodiments, the user interface 620 includes a display 622 and one or more user-selectable buttons (e.g., four buttons 624a, 624b, 624c, and 624d in this embodiment, a different arrangement of buttons in other embodiments, or touchscreen buttons in still other embodiments). The display 622 may include an active area in which numerals, text, symbols, images, or a combination thereof can be displayed. For example, the display 622 may be used to communicate a number of status indicators, alarms, settings, and/or menu options for the infusion pump system 600. In some embodiments, the display 622 can indicate inform the user of the amount of a suggested bolus dosage, the user's blood glucose level, an indication that the user's blood glucose level is rising or falling, an indication that the bolus dosage suggestion includes a correction for the rate of change in the user's blood glucose level, and the like.

In some embodiments, the user may press one or more of the buttons 624a, 624b, 624c, and 624d to shuffle through a number of menus or program screens that show particular status indicators, settings, and/or data (e.g., review data that shows the medicine dispensing rate, the amount of medicine delivered during the last bolus, the delivery time of the last bolus, the total amount of medicine dispensed in a given time period, the amount of medicine scheduled to be dispensed at a particular time or date, the approximate amount of medicine remaining in the cartridge 625, or the like). In some embodiments, the user can adjust the settings or otherwise program the pump assembly 660 by pressing one or more buttons 624a, 624b, 624c, and 624d of the user interface 620. For example, in embodiments of the infusion pump system 600 configured to dispense insulin, the user may press one or more of the buttons 624a, 624b, 624c, and 624d to change the dispensation rate of insulin or to request that a bolus of insulin be dispensed immediately or at a scheduled, later time. In another example, the user may use the buttons 624a-d to manually input information such as the user's current blood glucose level (e.g., as measured by an external blood glucose meter), the current rate of change in the user's blood glucose level, or the like into the pump system 600.

The pump assembly 660 also includes a NFC circuit 640. The NFC circuit 640 can wirelessly communicate with external NFC tags, such as example NFC tags 646a, 646b, 646c, and 646d. As described previously, such wireless communications using NFC technology can enhance and simplify user interactions with the infusion pump system 600. For instance, using NFC, the need for user activation of buttons 624a-d for shuffling through menus may be reduced in some circumstances. FIG. 6 depicts an example scenario to illustrate this operational concept. In this example scenario, the user of infusion pump system 600 has consumed, or will soon consume, about 20 grams of carbohydrates. As such, the user desires to initiate a corresponding bolus dispensation of insulin to counteract the effects of the intake of 20 grams of carbohydrates. The bolus dispensation of insulin is intended to cause the user's blood glucose level to remain within a target range. To initiate the desired bolus dispensation, the user first positions the pump assembly 660 containing the NFC circuit 640 in close proximity with the NFC tag 646b (which is programmed to correspond to 20 grams of carbohydrates). Wireless NFC communications can thereby be established between the NFC circuit 640 and the NFC tag 646b (as signified by wireless communication symbol 641). In some embodiments, the user is provided with a notification that NFC communications have been established. The notification can be visual, audible, tactile, and a combination thereof. In some embodiments, in response to the communication from the NFC tag 646b to the pump assembly 660, the pump assembly 660 provides a prompt to the user on the display device 622. In this example, the prompt on the display device 622 requests the user to confirm that the user desires to receive a 1.3 unit dispensation of insulin because of the intake of 20 grams of carbohydrates. To confirm the dispensation of the suggested bolus amount, the user can simply press the button 624d directly below the word "Enter." By this example, it can be appreciated that the incorporation of NFC technology in the infusion pump system 600 can enhance and simplify user interactions with the infusion pump system 600, because to initiate an appropriate bolus dosage of insulin the user simply had to present a NFC tag 646b to the NFC circuit 640 and then press button 624d in response to the prompt on the display device 622.

Optionally, the pump assembly 660 can further include at least one accelerometer 650. In some embodiments, the accelerometer 650 can be used to activate or complete the NFC communications when a characteristic value of a detected movement of the pump assembly 660 is at or above the threshold level, as previously described above in connection with FIGS. 1 and 4. In such circumstances, the control circuitry housed in the pump assembly 660 be configured to determine when the housing 610 is "bumped" against one of the NFC tags 646a-d so as to activate the NFC transmission via the NFC circuit 640.

Figure 7:
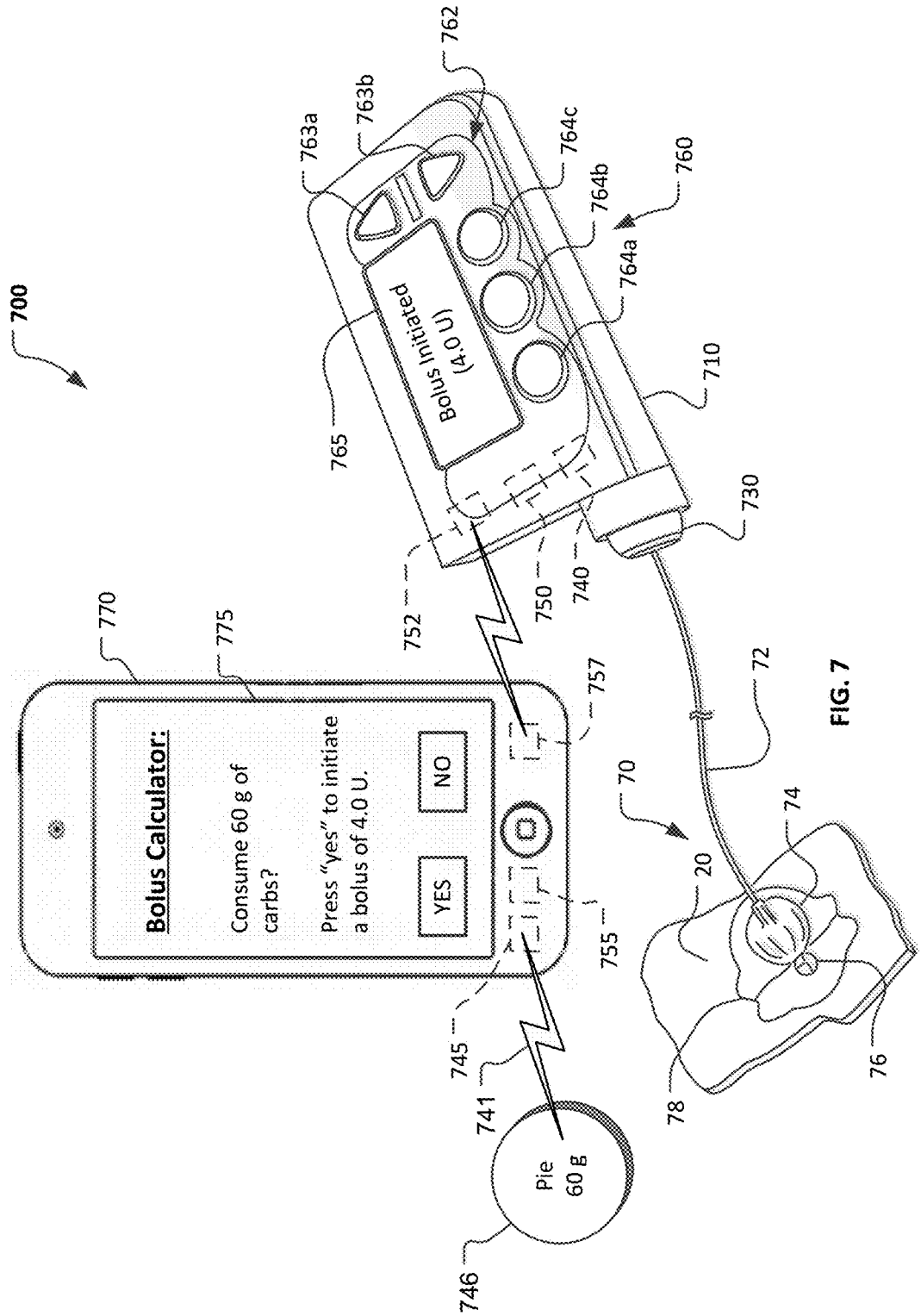
FIG. 7 is a perspective view of another infusion pump system with NFC capabilities in accordance with some embodiments.

Referring now to FIG. 7, some embodiments of an infusion pump system 700 an can include an ancillary remote control device 770 configured to communicate with NFC tags 746 and with a pump assembly 760. In this example embodiment, the remote control device 770 is a smartphone. In other embodiments, the remote control device 770 can be other types of devices such as a tablet computer, laptop computer, a PDA, a custom remote device manufactured specifically for interfacing with the pump assembly 760, and the like. In this example embodiment, the pump assembly 760 is a single-piece pump unit (similar to the embodiment described above in connection with FIG. 1). In other embodiments of the infusion pump system 700, the pump assembly 760 can be configured as a two-piece pump assembly such as the example depicted in FIG. 5.

In general, the remote control device 770 includes a control system for controlling the infusion pump assembly 760, including user interface components such as touchscreen user interface 775 for allowing a user to receive and provide instructions relative to the infusion pump assembly 760. The remote control device 770 also includes a wireless interface 757 for communicating with a wireless interface 752 of the pump assembly 760. The wireless interfaces 752 and 757 for communicating between the pump assembly 760 and the remote control device 770 can utilize any of a variety of wireless communication technologies, such as Bluetooth, WiFi, RF, infrared, ultrasonic, electromagnetic induction, NFC, or combinations thereof. The pump assembly 760 can be used to dispense insulin or another medication to a user via, for example, an infusion set 70 as described in regard to other infusion pump system embodiments herein.

In this embodiment, the pump assembly 760 includes a housing structure 710 that defines a cavity in which a fluid cartridge (e.g., an insulin carpule or other medicine cartridge) can be received. The pump assembly 760 also includes a cap device 730 to retain the fluid cartridge in the cavity of the housing structure 710. The pump assembly 760 includes a drive system (e.g., described in more detail in connection with FIG. 5) that advances a plunger in the fluid cartridge so as to dispense fluid therefrom. In some embodiments, the dispensed fluid exits the fluid cartridge, passes through a flexible tube 72 of the infusion set 70 to a cannula housing 74. The dispensed fluid can enter through the skin 20 via a cannula 76 attached to the underside of the cannula housing 74.

In some embodiments, the infusion pump system 700 can be configured to supply scheduled basal dosages of insulin (or another medication) along with user-selected bolus dosages. The basal delivery rate can be selected to maintain a user's blood glucose level in a targeted range during normal activity when the user is not consuming food items. The user-selected bolus deliveries may provide substantially larger amounts of insulin in particular circumstances, such as when the user consumes food items, when the user's blood glucose level increases beyond a safe limit, when the user's blood glucose level rises faster than a threshold rate, or other scenarios in which the blood glucose level requires a significant correction. In some embodiments, the infusion pump system 700 may modify a bolus delivery (e.g., a bolus delivery after the user consumes a meal) in response to certain circumstances. For example, the infusion pump system 700 may decrease or otherwise modify a post-meal bolus delivery based on a rapidly falling blood glucose level, a current blood glucose level that is below a threshold limit, a detection of a high level of physical activity, or the like.

Still referring to FIG. 7, in this embodiment, the pump assembly 760 includes the user interface 762 that permits a user to monitor the operation of the pump assembly 760. In some embodiments, the user interface 762 includes a display 765 and one or more user-selectable buttons (e.g., five buttons 764a, 764b, 764c, 763a, and 763b in this embodiment). The display 765 may include an active area in which numerals, text, symbols, images, or a combination thereof can be displayed. For example, the display 765 may be used to communicate a number of status indicators, alarms, settings, and/or menu options for the infusion pump system 700. In some embodiments, the display 765 can indicate inform the user of the amount of a suggested bolus dosage, the user's blood glucose level, an indication that the user's blood glucose level is rising or falling, an indication that the bolus dosage suggestion includes a correction for the rate of change in the user's blood glucose level, and the like.

In some embodiments, the user may press one or more of the buttons 764a, 764b, 764c, 763a, and 763b to shuffle through a number of menus or program screens that show particular status indicators, settings, and/or data (e.g., review data that shows the medicine dispensing rate, the amount of medicine delivered during the last bolus, the delivery time of the last bolus, the total amount of medicine dispensed in a given time period, the amount of medicine scheduled to be dispensed at a particular time or date, the approximate amount of medicine remaining in the cartridge, or the like). In some embodiments, the user can adjust the settings or otherwise program the pump assembly 760 by pressing one or more buttons 764a, 764b, 764c, 763a, and 763b of the user interface 762. For example, in embodiments of the infusion pump system 700 configured to dispense insulin, the user may press one or more of the buttons 764a, 764b, 764c, 763a, and 763b to change the dispensation rate of insulin or to request that a bolus of insulin be dispensed immediately or at a scheduled, later time. In another example, the user may use the buttons 764a, 764b, 764c, 763a, and 763b to manually input information such as the user's current blood glucose level (e.g., as measured by an external blood glucose meter), the current rate of change in the user's blood glucose level, or the like into the pump system 700.

As an alternative to, or in addition to, using user interface 762 to control the pump assembly 760, the remote control device 770 can be used to control the pump assembly 760 in this embodiment. Such an arrangement may be convenient, for example, if the user is wearing the pump assembly 760 in a concealed location under clothing. The remote control device 770 can wirelessly communicate with the pump assembly 760 via the wireless interfaces 757 and 752. The wireless communications between the pump assembly 760 and the remote control device 770 can utilize any of a variety of wireless communication technologies, such as Bluetooth, WiFi, RF, infrared, ultrasonic, electromagnetic induction, NFC, and the like, and combinations thereof. Using remote control device 770, a user can enter and receive information whereby the user can control the pump assembly 760 using the touchscreen user interface 775 of the remote control device 770 as an alternative to, or in addition to, using the user interface 762 of the pump assembly 760. In some alternative embodiments, the pump assembly 760 may be configured without a user interface display 765 or other user interface components for purposes of reducing manufacturing costs, in which case the user interface 775 of the remote control device 770 would serve as the user interface for the system 700.

The remote control device 770 also includes a NFC circuit 745. The NFC circuit 745 can wirelessly communicate with external NFC tags, such as the example NFC tag 746. As described previously, such wireless communications using NFC technology can enhance and simplify user interactions with the infusion pump system 700. For instance, using NFC, the need for user activation of buttons 764a, 764b, 764c, 763a, and 763b, or for using user the touchscreen user interface 775, for shuffling through menus may be reduced in some circumstances. FIG. 7 depicts an example scenario to illustrate this principle. In this example scenario, the user of infusion pump system 700 has consumed, or will soon consume, about 60 grams of carbohydrates by eating a piece of pie. As such, the user desires to initiate a corresponding bolus dispensation of insulin to counteract the effects of the intake of 60 grams of carbohydrates. The bolus dispensation of insulin is intended to cause the user's blood glucose level to remain within a target range. To initiate the desired bolus dispensation, the user first positions the remote control device 770 containing the NFC circuit 745 in close proximity with the NFC tag 746 (which is programmed to correspond to 60 grams of carbohydrates). Wireless NFC communications can thereby be established between the NFC circuit 745 and the NFC tag 746 (as signified by wireless communication symbol 741). In some embodiments, the user is provided with a notification that NFC communications have been established. The notification can be visual, audible, tactile, and a combination thereof.

In response to the communication from the NFC tag 746 to the remote control device 770, the remote control device 770 can provide a prompt to the user on the touchscreen user interface 775. In this example, the prompt on the touchscreen user interface 775 requests the user to confirm whether the user desires to receive a 4.0 Unit dispensation of insulin because of the intake of 60 grams of carbohydrates. To confirm the dispensation of the suggested bolus amount, the user can simply touch the portion of the touchscreen user interface 775 that is labeled "YES." Or, the user can decline the dispensation of the suggested bolus amount by touching the portion of the touchscreen user interface 775 that is labeled "NO." By this example, it can be appreciated that the incorporation of NFC technology in the infusion pump system 700 can enhance and simplify user interactions with the infusion pump system 700, because to initiate an appropriate bolus dosage of insulin the user simply had to present a NFC tag 746 to the NFC circuit 745 of the remote control device 770 and then touch the portion of the touchscreen user interface 775 that is labeled "YES."

Optionally, the remote control device 770 can further include at least one accelerometer 755. In some embodiments, the accelerometer 755 can be used to activate the NFC communications when a characteristic value of a detected movement of the remote control device 770 is at or above the threshold level, as previously described above in connection with FIGS. 1 and 4. In such circumstances, the control circuitry housed in remote control device 770 be configured to determine when the remote control device 770 is "bumped" against one of the NFC tags 746 so as to activate the NFC transmission via the NFC circuit 745.

While the infusion pump system 700 includes the remote control device 770 that includes NFC circuit 745, in some embodiments the pump assembly 760 can also include a NFC circuit 740. Therefore, the user can alternatively present NFC tags to the pump assembly 760 to input information to the pump assembly 760. Similarly, the pump assembly 760 can optionally include at least one accelerometer 750 that can be used to activate the NFC communications when a characteristic value of a detected movement of the pump assembly 760 is at or above the threshold level, as previously described above in connection with FIGS. 1 and 4. In such circumstances, the control circuitry housed in pump assembly 760 be configured to determine when the pump assembly 760 is "bumped" against one of the NFC tags 746 so as to activate the NFC transmission via the NFC circuit 740.

A number of embodiments of the invention have been described. Nevertheless, it will be understood that various modifications may be made without departing from the spirit and scope of the invention. Accordingly, other embodiments are within the scope of the following claims.

What is claimed is:

1. A medical infusion pump system, comprising:
    a portable pump comprising:
    a portable housing defining a space to receive a medicine;
    a pump drive system to dispense medicine from the portable housing when the medicine is received in the space;
    control circuitry that communicates control signals to the pump drive system to control dispensation of the medicine from the portable housing when the medicine is received in the space;
    a first near field communication (NFC) circuit electrically connected with the control circuitry to communicate infusion pump task data to the control circuitry, wherein the first NFC circuit is configured to wirelessly receive the infusion pump task data from at least one of a plurality of NFC communicator devices, wherein each of the plurality of NFC communicator devices stores respective infusion pump task data, wherein first infusion pump task data that are stored in a first NFC communicator device of the plurality of NFC communicator devices are transferred from the first NFC communicator device of the plurality of NFC communicator devices when the first NFC circuit and the first NFC communicator device are positioned within a NFC proximity range; and
    a wireless communication device different from the first NFC circuit connected to the control circuitry; and
    a remote control device that is separate from the portable pump, the remote control device being configured to wirelessly communicate with the wireless communication device connected to the control circuitry, and the remote control device comprising a second NFC circuit, wherein the remote control device is configured to prompt a user to deliver a bolus dispensation of the medicine when the second NFC circuit and a second NFC communicator device of the plurality of NFC communicator devices are positioned within the NFC proximity range, the bolus dispensation of the medicine is based on second infusion pump task data that are stored in the second NFC communicator device of the plurality of NFC communicator devices.

2. The medical infusion pump system of claim 1, wherein the portable pump further comprises an accelerometer electrically connected to the control circuitry, wherein the accelerometer is configured to detect acceleration movement of the portable pump and to communicate the detected movement to the control circuitry, and wherein the control circuitry is configured to compare a characteristic value of the detected movement to a threshold movement value.

3. The medical infusion pump system of claim 2, wherein the control circuitry is configured to activate near field communication between the first NFC circuit and at least one of the plurality of NFC communicator devices based on the comparison of the characteristic value to the threshold movement value.

4. The medical infusion pump system of claim 1, wherein the plurality of NFC communicator devices are a plurality of NFC tags.

5. The medical infusion pump system of claim 4, wherein the infusion pump task data comprises a unique identifier that identifies a particular NFC tag of the plurality of NFC tags, and wherein, in response to receiving the unique identifier, the control circuitry executes one or more user interface operations that correspond to the unique identifier.

6. The medical infusion pump system of claim 5, wherein the user interface operations comprise configuring user interface settings for calculating the bolus dispensation of the medicine.

7. The medical infusion pump system of claim 4, wherein each of the plurality of NFC tags stores different infusion pump task data.

8. The medical infusion pump system of claim 7, wherein infusion pump task data stored on at least one of the plurality of NFC tags include an indication of an amount of carbohydrates consumed.

9. The medical infusion pump system of claim 7, wherein infusion pump task data stored on at least one of the plurality of NFC tags include an indication of a particular food consumed.

10. The medical infusion pump system of claim 7, wherein infusion pump task data stored on at least one of the plurality of NFC tags include an indication of a type of meal consumed.

11. The medical infusion pump system of claim 7, wherein infusion pump task data stored on at least one of the plurality of NFC tags include an indication of an activity performed by the user of the medical infusion pump system.

12. The medical infusion pump system of claim 1, wherein the second NFC circuit is configured to wirelessly receive the second infusion pump task data from the second NFC communicator device when the second NFC circuit and the second NFC communicator device are positioned within the NFC proximity range.

13. The medical infusion pump system of claim 1, wherein the NFC proximity range has a maximum working distance of less than 12 inches.

14. The medical infusion pump system of claim 1, wherein the infusion pump task data is indicative of a value of carbohydrates of a food item.

15. The medical infusion pump system of claim 1, wherein each of the plurality of NFC communicator devices contains different infusion pump task data.

16. The medical infusion pump of claim 1, wherein the first NFC communicator device of the plurality of NFC communicator devices is different from the second NFC communicator device of the plurality of NFC communicator devices.

17. An insulin delivery system, comprising: an insulin delivery device comprising (a) a pump housing that defines a space to receive a medicine and (b) a drive system positioned in the pump housing to dispense the medicine from the pump housing when the medicine is received in the space of the pump housing; a controller device removably attachable to the pump housing, the controller device comprising a first near field communication (NFC) circuit electrically connected with control circuitry configured to communicate control signals to the drive system, the first NFC circuit configured to communicate information related to the treatment of diabetes to the control circuitry, wherein the first NFC circuit is configured to wirelessly receive the information related to the treatment of diabetes from at least one of a plurality of NFC communicator devices, wherein each of the plurality of NFC communicator devices stores respective information related to the treatment of diabetes, wherein particular information related to the treatment of diabetes that is stored in a first NFC communicator device of the plurality of NFC communicator devices is transferred from the first NFC communicator device of the plurality of NFC communicator devices when the first NFC circuit and the first NFC communicator device are positioned within a NFC proximity range, the controller device further comprising a user interface comprising one or more input components and output components that are electrically connected to the control circuitry, wherein the controller device is adapted to prompt an insulin dosage recommendation based on the particular information related to the treatment of diabetes in response to wirelessly receiving the particular information related to the treatment of diabetes; and a remote control device that is separate from the controller device, the remote control device being configured to wirelessly communicate with the controller device, and the remote control device comprising a second NFC circuit, wherein the remote control device is configured to prompt a user to deliver a bolus dispensation of the medicine when the second NFC circuit and a second NFC communicator device of the plurality of NFC communicator devices are positioned within the NFC proximity range, wherein the bolus dispensation of the medicine is based on additional information related to the treatment of diabetes that is stored in the second NFC communicator device of the plurality of NFC communicator devices.

18. The insulin delivery system of claim 17, wherein the plurality of NFC communicator devices are a plurality of NFC tags.

19. The insulin delivery system of claim 17, wherein each of the plurality of NFC communicator devices contains different information related to the treatment of diabetes.

20. The insulin delivery system of claim 19, wherein the information related to the treatment of diabetes stored by at least some of the NFC communicator devices is an indication of an amount of carbohydrates consumed.

* * * * *